US010918839B2

(12) United States Patent
Mayda, II

(10) Patent No.: US 10,918,839 B2
(45) Date of Patent: Feb. 16, 2021

(54) BALLOON CATHETER

(71) Applicant: Jaro Mayda, II, Lewisville, TX (US)

(72) Inventor: Jaro Mayda, II, Lewisville, TX (US)

(73) Assignee: Jaro Mayda, II, Lewisville, TX (US)

( * ) Notice: Subject to any disclaimer, the term of this patent is extended or adjusted under 35 U.S.C. 154(b) by 365 days.

(21) Appl. No.: 15/919,451

(22) Filed: Mar. 13, 2018

(65) Prior Publication Data
US 2019/0282789 A1 Sep. 19, 2019

(51) Int. Cl.
*A61M 25/10* (2013.01)

(52) U.S. Cl.
CPC ........ *A61M 25/10* (2013.01); *A61M 25/1029* (2013.01); *A61M 2025/105* (2013.01); *A61M 2025/1031* (2013.01); *A61M 2025/1086* (2013.01)

(58) Field of Classification Search
CPC .............. A61M 25/10; A61M 25/1029; A61M 2025/1031; A61M 2025/105; A61M 2025/1086; A61M 2025/1072; A61M 5/1408; A61M 5/2066; A61M 5/2448; A61M 5/3291; A61M 5/282; A61M 37/0015; A61M 2037/0023
See application file for complete search history.

(56) References Cited

U.S. PATENT DOCUMENTS

| | | | |
|---|---|---|---|
| 2,944,549 A * | 7/1960 | Alexander | A61M 5/282 604/195 |
| 6,086,562 A * | 7/2000 | Jacobsen | A61M 5/14248 604/131 |
| 6,398,757 B1 | 6/2002 | Varenne et al. | |
| 6,638,246 B1 * | 10/2003 | Naimark | A61M 25/10 604/103 |
| 7,547,294 B2 | 6/2009 | Seward et al. | |
| 8,538,515 B2 | 9/2013 | Atanasoska et al. | |
| 8,556,849 B2 | 10/2013 | Consigny et al. | |
| 8,740,843 B2 | 6/2014 | Eaton et al. | |
| 9,393,386 B2 | 7/2016 | Schneider et al. | |
| 9,414,946 B2 | 8/2016 | Gittard | |
| 9,486,431 B2 | 11/2016 | McClain et al. | |
| 9,510,856 B2 | 12/2016 | McClain et al. | |
| 2003/0065303 A1 * | 4/2003 | Wellman | A61M 29/02 604/500 |
| 2003/0135161 A1 * | 7/2003 | Fleming | A61B 5/150984 604/173 |
| 2005/0273075 A1 * | 12/2005 | Krulevitch | A61M 37/0015 604/509 |

(Continued)

*Primary Examiner* — Manuel A Mendez
*Assistant Examiner* — Justin L Zamory
(74) *Attorney, Agent, or Firm* — International IP Law Group, PLLC

(57) ABSTRACT

The present application regards examples of a fluid delivery device including a spike including a base end and a pointed end, an inlet opening located along the shaft of the spike between the base end and the pointed end, and an outlet opening located on the pointed end. In an example, the fluid delivery device includes an inner flexible layer, wherein the base end of the spike is attached to the inner flexible layer. The fluid delivery device includes an outer flexible layer, wherein the spike punctures the outer flexible layer in response to the inner flexible layer moving towards the outer flexible layer in response to inflation of a volume of space enclosed by the inner flexible layer.

19 Claims, 20 Drawing Sheets

(56) References Cited

U.S. PATENT DOCUMENTS

2010/0042121 A1* 2/2010 Schneider ......... A61M 25/1027
606/159
2011/0166516 A1* 7/2011 Orr ................... A61M 25/1002
604/103.01

* cited by examiner

100

200

700

800

1300

1400

1500

1700

BALLOON CATHETER

BACKGROUND

A balloon catheter is a type of catheter with an inflatable balloon at its tip which is used during a catheterization procedure to enlarge a narrow opening or passage within the body. The deflated balloon catheter is positioned by insertion into a vessel such as a blood vessel. Once positioned, the balloon is then inflated to widen the opening before the balloon is then deflated again in order to be removed.

BRIEF DESCRIPTION OF THE DRAWINGS

Certain examples are described in the following detailed description and in reference to the drawings, in which.

DETAILED DESCRIPTION OF SPECIFIC EXAMPLES

Figure 1:
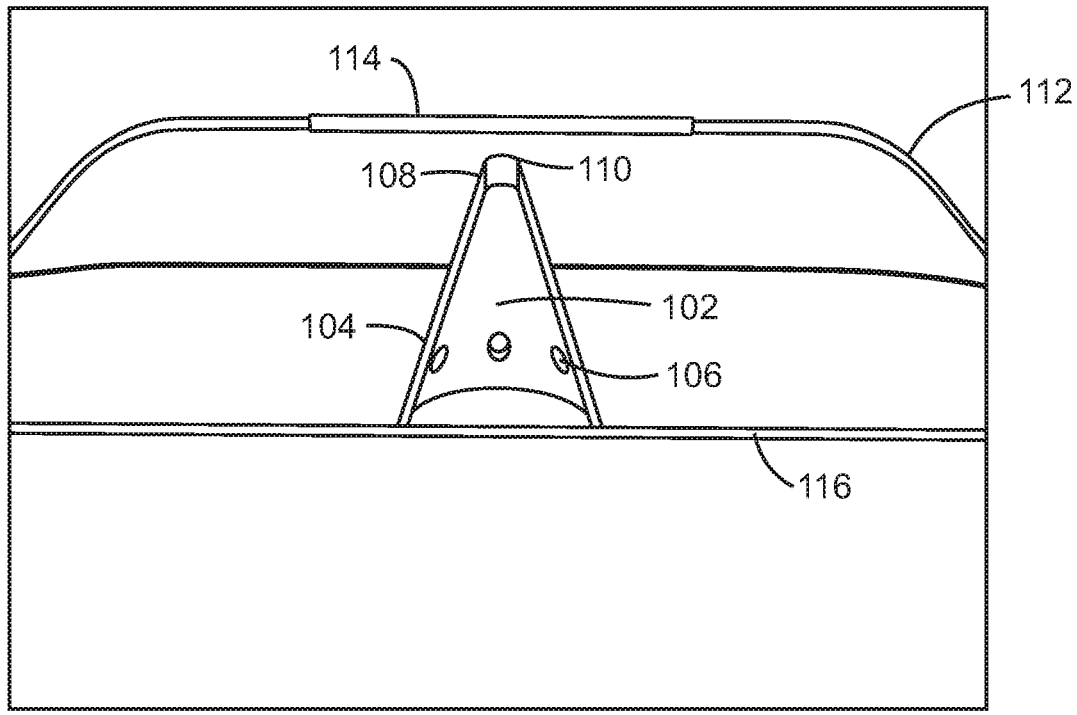
FIG. 1 is a diagram of a blister configuration of a balloon catheter.

The disclosed balloon catheter may be employed, for example, in the treatment of occluded vessels. Examples of occluded vessels include arteries and veins, but could also include other types of vessels including urinary vessels or other biological channels of varying sizes and scales.

In an example, the balloon catheter may be used in vessels such as arteries to widen the vessel or to remove or destroy or break up a plaque deposit on the vessel. The process of arterial narrowing, called stenosis, and total blockage, called occlusion, involves changes in the intima layer of an artery which allows for disruption and changes in the media layer of the artery with accumulation of cholesterol, lipids, proteins, calcium, etc. and which, through a sheer mass effect of matter accumulation, leads to occlusion. This collection of debris can collectively be referred to as a plaque deposit in this disclosure no matter the exact compositional makeup of the blockage in question.

In an example, the disclosed balloon catheter can inflate and physically break up the atheroma as well as eject fluid such as medication into the occupied by the atheroma and accelerate the dissolution of the atheroma. Dissolution of the atheroma results in a clean artery without significant plaque. The presently disclosed balloon catheter avoids a need for stents to maintain the reconstituted channel after atherectomy and/or balloon angioplasty due to the precision of medication delivery.

The disclosed balloon includes two configurations, the blister configuration and the porcupine configuration. The blister configuration involves a balloon catheter with blister packs attached to the surface. These blister packs contain a sealed space containing a spike at the base of the blister. The spike is not in contact with the top surface of the blister in a pre-inflated state. The fluid contained in the blisters can vary according to the needs of the patient and are pre-filled at manufacturing. As the blister configuration balloon expands, direct pressure is applied by the plaque or the vessel onto the top of the blister pack pushing it down toward the spike. The spike perforates the blister resulting in the ejection of the blister contained fluid into the plaque to aid the dissolution of the plaque.

The porcupine configuration includes a balloon catheter having two layers of balloons with spikes mounted on the inner balloon layer. The spikes may be mounted on a platform of the inner balloon layer or maybe contained in reverse blister compartments attached to the inner balloon layer. In an example of the reverse blister compartments, the reverse blisters are prefabricated and inserted into holes drilled in the inner balloon wall and glued or welded in place. The second and outer layer of the balloon in a porcupine configuration is placed over the inner layer and spot welded to the inner balloon layer in rows. The spot welding of the inner and outer layers results in continuous columns of space between the two adjacent columns of welded plastic. In an example, the inner balloon has an inflation channel. The outer balloon would have an infusion channel to allow fluid to flow through the channel. The inner balloon may be inflated when in position for the atheroma being treated or vessel being injected into. The inflation of the inner balloon layer may initially cause both inner and outer balloons to inflate at the same rate. In an example, the outer balloon layer inflates until touching the atheroma. The outer balloon may be made of a non-compliant or semi-compliant and flexible material to allow the outer balloon layer to expand to a specific limited diameter. The inner balloon may be semi-compliant or compliant and more flexible than the outer balloon layer. When the outer layer is expanded to a maximal diameter, continued inflation of the inner balloon would push the spikes of the inner balloon through the outer balloon and into the plaque. In an example where the inner layer included reverse blisters installed in the inner balloon layer, then the inflation would cause the spikes to puncture both the reverse blister as well as the outer layer.

In an example, the inner balloon of a porcupine configuration of a balloon catheter includes rows of spikes at different degrees of coverage around the circumference of the balloon. Some examples could include complete circumferential coverage while others would involve 60-180 degrees of the surface. In those balloon with less than complete coverage by the spikes, there would may be three directional markers lengthwise on the balloon indicating beginning, end and midpoint of the spiked balloon area so that placement can be seen through ultrasonic, laser, or x-ray analysis searching for the lengthwise markers. In an example, another set of directional markers could indicate various sides and directions of the balloon catheter.

In an example, the blisters and reverse blisters can contain contrast such as non-iodinated contrast. When using contrast, there would be visual confirmation that the spikes were in the proper location after perforating the outer layer of the balloon casing and entering a target lesion such as arterial plaque. Contrast stored in the blister and reverse blister and later deployed by the spikes could also indicate that there has not been perforation of the outer layer of the vessel being treated. In an example, fluid in a porcupine configuration can be pushed into the space between the inner and outer layers, then through the spikes towards a target area such as the plaque or specific layer of a vessel.

Once a balloon catheter has been used, the balloon may be deflated and removed. In an example, a single balloon with a single spike could be used to test the plaque before placing a balloon with a full column of spikes. The depth of penetration of a spike or row of a plurality of spikes could vary according to the size of the spike in diameter and length. X-ray and ultrasound guidance can be used in selecting a balloon catheter configuration and fluid to be deployed. Further, in some examples, the balloon of the balloon catheter could also be made with an ultrasound or laser imaging system attached at the end of the balloon catheter to enable imaging the spikes in real time.

FIG. 1 is a diagram of a blister configuration 100 of a balloon catheter. The blister configuration 100 of a balloon catheter includes a spike 102 used to deliver fluid to puncture the blister and deliver fluid to a target region. The spike 102 can be a hollow cone shape, needle shape, or other shape capable of puncturing a blister and allowing flow of fluid. In an example, the spike 102 may serve one or more purposes including puncturing a flexible layer, guiding and ejecting fluid in an indicated direction, piercing a physical plaque deposit, piercing into a particular level of a blood vessel, fluid ejection into a particular layer of a blood vessel, or piercing a target area in order to anchor the balloon catheter into a specific place.

The spike 102 can include a spike shaft 104 which refers to a longer portion of the spike 102 through which fluid may travel through a spike inlet 106 towards the spike pointed end 108. The spike pointed end 108 is a narrower portion of the spike 102 when compared to the spike shaft 104 such that the spike pointed end 108 can puncture through a blister of a balloon catheter. The spike pointed end 108 can have a spike outlet 110 centered on the end of the spike pointed end 110 or slightly off-center of the spike pointed end 108 so that the spike pointed end 108 includes a joining of the sides of the spike 102 in a single point. In an example the spike 102 can include a base end which is opposite the spike pointed end 108 and may be a wider portion of the spike 102. In an example where the spike 102 has a shaft diameter that is the same from pointed end to based, the base end and the pointed end may have the same diameter. The spike outlet 110 is large enough that fluid can flow through it in a direction indicated to be approximately parallel with a direction of fluid flow through the spike shaft 104 towards the spike outlet 110.

The spike 102 can be encased by blister casing 112 which includes a puncture region 114 located over the spike 102. The blister casing 112 can be connected to the blister base 116 through lamination, adhesive, physical linking, or other means. The connection of the blister casing 112 to the blister base 116 is sufficient to prevent fluid inside the blister casing 112 from leaking prior to the spike 102 puncturing through the puncture region 114. The fluid inside blister can be medication, indicator, saline, reagent, a dissolving agent, a fluid used to erode plaque through physical abrasion, or any other a solution containing an intended product through the spike and towards a target region. In an example, the target region may be inside an artery or other vessel or region a catheter may be used.

The puncture region 114 may be the same material as the blister casing 112 or may be a different material more prone to puncturing. In an example, the blister casing 112 is a flexible material such as a plastic or other synthetic material. The blister base 116 can be connected to the spike 102 by the spike base end so that the spike base end has a more diffuse pressure profile on the blister base 116 than the spike pointed end 108. This difference in the shape of the spike 102 at different ends ensures a pressure pushing the blister casing 112 towards the spike pointed end 108 would allow the spike 102 to puncture the puncture region while the spike 102 experiencing the pressure of the blister casing 112 would not puncture the blister base 116. In an example, the blister base 116 is a similar material to the blister casing 112 or the same material as the blister casing 112. The blister base may be a flexible material and may be thicker than the blister casing 112 to ensure the blister casing 112 punctures in response to pressure applied from the blister casting 112 towards the spike 102.

In response to pressure being applied to the blister casing 112 pushing the blister casing towards the spike 102, the blister casing may puncture at the puncture region 114 as the spike pointed end 108 and spike outlet puncture and pass through the puncture region 114 of the blister casing 112. In response to blister casing being pressed towards the spike 102 and the blister base 116, the volume inside the blister may decrease thereby increasing an internal pressure on the fluid held between the blister casing 112 and blister base 116. In response to the spike 102 puncturing puncture region 114, the fluid inside the blister may travel through the spike 102 due to the increased internal pressure between the blister casing 112 and blister base 116. A fluid flow in a puncture blister would flow from inside the region formed by the blister casing 112 and the blister base 116 into the spike 102 through one or more spike inlet 106, then travel through the spike 102 and exit the spike outlet 110. As the spike outlet 110 in punctured blister would be outside of the region encased by the blister casing 112 and the blister base 116, the fluid could be ejected into a vessel target region such as a vessel blockage such as plaque.

In an example, the spike 102 may be pressed into a layer of the vessel itself such as the intima, media, or between layers such as between the intima and media, or between the media and the adventitia. A spike 102 lodged into plaque and ejecting fluid may make use of both the spike as a physical means of agitating and breaking up the plaque to allow plaque to be carried away thus reducing the size of a vessel blockage. In an example, the spike 102 may be lodged into plaque of a vessel and the ejected fluid from inside the blister may be a specific fluid targeted to aid in destroying, dissolving, or otherwise breaking up the plaque. In an example, the spike 102 may be lodged into a part of the vessel and may eject fluid that has an effect on the vessel itself such as an anti-inflammatory medicine, a biological agent that alters the function and structure of the vessel, or specific vitamins, nutrients, or other chemicals that provide the vessel a localized delivery of these agents.

Figure 2:
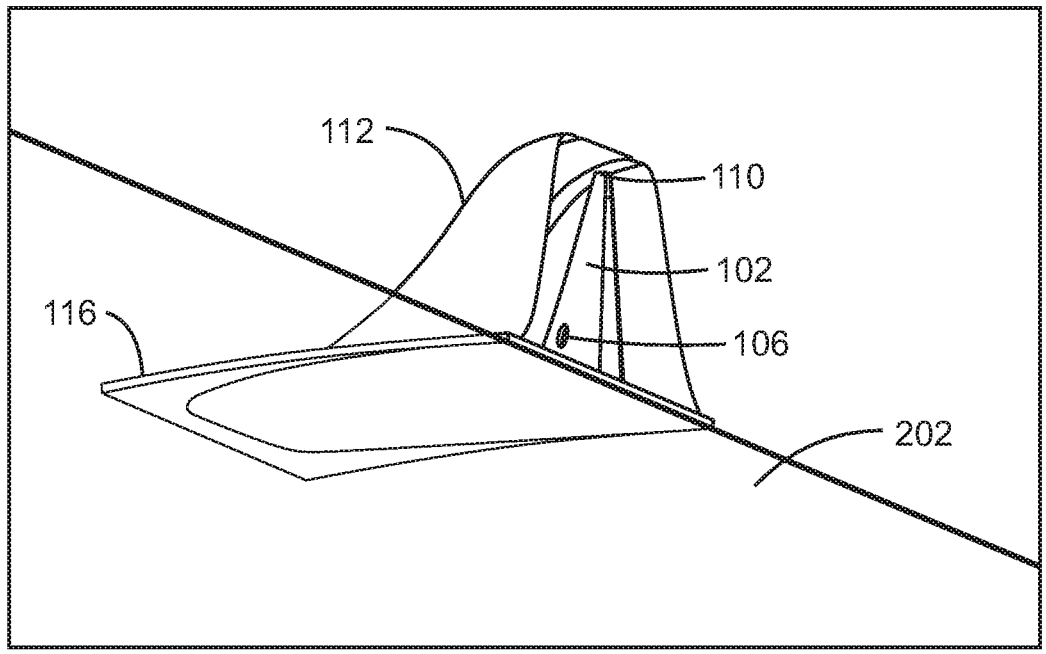
FIG. 2 is a side view of a blister configuration of a balloon catheter.

FIG. 2 is a side view of a blister configuration 200 of a balloon catheter. Like numbered items are as disclosed with respect to FIG. 1 above. The side view allows illustration of the blister configuration 200 in a balloon catheter in an unpunctured state.

The blister base 116 may be affixed or a part of the balloon casing 202 of the balloon catheter. Generally speaking the balloon casing 202 refers to the material of a balloon that is filled, stretches, and expands when inflated. In a balloon catheter, the balloon region of the catheter may be mounted on a catheter which is inserted into a region such as a blood vessel or other biological region or cavity where a catheter may be useful. The balloon casing 202 may be a flexible material that the spike 102 is attached to. To this effect, the balloon casing 202 is shown here in close up as a region of the balloon that may be expanded when inflated and accordingly move the blister, and fluid contained in the blister, and the spike 102 towards a target area inside of a vessel or other cavity. The balloon casing 202 may be a flexible material that is part of the balloon catheter and expands in response to the inflation of the balloon catheter. In an example, the blister base 116 and the balloon casing may be the same material, in which case the drawings and figures would merely refer to specific regions of that material where a blister casing 112 was attached in the case of the blister base 116 or where the blister casing 112 was not attached, i.e. the balloon casing 202. In cases where the blister base 116 and the balloon casing are separate elements that are connected, the blister base 116 may be laminated, adhered, or otherwise affixed to the balloon casing 202. As the balloon catheter is expanded, the balloon casing 202 may press outward thus generating a force that presses the blister casing 112 both against a vessel wall or target area such as a collection of plaque. As disclosed above, the pressure of the blister casing 112 against the vessel wall or plaque would press the blister casing 112 towards the spike 102. In an example, the balloon casing 202 would continue to press the blister base 116 and thus the spike 102 further outward towards the blister casing 112 as the balloon catheter expanded. Continued balloon catheter expansion will result in the balloon casing 202 and thus the blister base 116 pushing the spike 102 towards the blister casing 112 eventually puncturing the blister casing 112 if the blister casing 112 is stuck against a vessel wall. As disclosed above, once the blister casing is punctured, the fluid inside the blister may pass into the spike inlet 106, through the spike 102, out the spike outlet 110, toward the target area.

Figure 3:
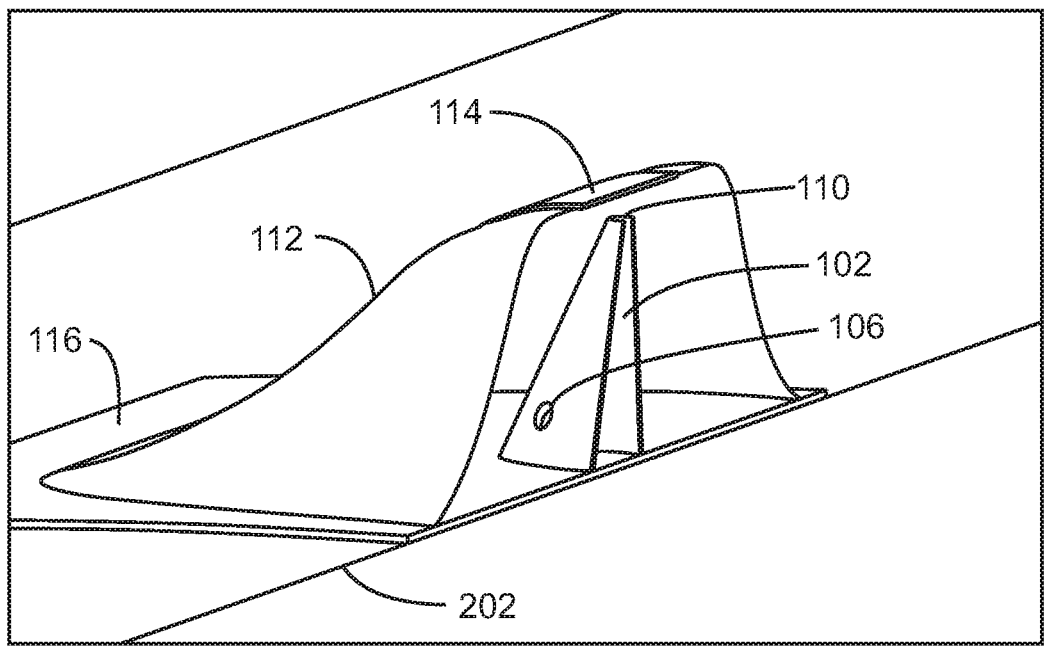
FIG. 3 is a diagram of a blister mounted on a balloon catheter.

FIG. 3 is a diagram of a blister mounted on a balloon catheter 300. Like numbered items are as shown above. The view from above the blister on a balloon casing 202 of a balloon catheter shows an unpunctured blister where the blister casing 112 is not physically touching the spike outlet 110. When the spike 102 is not touching the blister casing 112 then the spike cannot puncture the puncture region 114. The physical separation of the spike 102 and the blister casing 112 can be accomplished by filling the region between the blister casing 112 and the blister base 116 with the fluid disclosed above that is ejected towards a target region of the balloon catheter. The amount of fluid between the blister casing 112 and the blister base 116 could fill the cavity such that the blister casing 112 did not touch the spike 102 and also did not break the connection between the blister casing 112 and the blister base 116.

Figure 4:
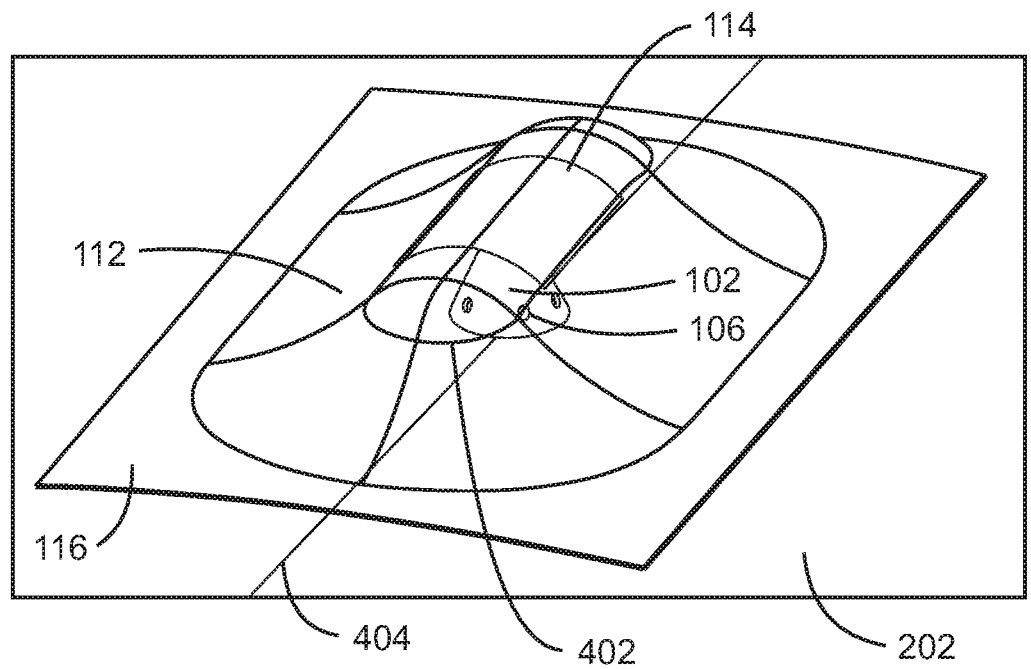
FIG. 4 is a diagram of a blister configuration of a balloon catheter in an oval shape and aligned along an insertion direction.

FIG. 4 is a diagram of a blister configuration of a balloon catheter in an oval shape 400 and aligned along an insertion direction. Like numbered items are as disclosed above.

As discussed above, a catheter may be inserted into a blood vessel or other tubular cavity. As the blister casing 112 and spike 102 extend beyond the surface of the balloon casing 202 these elements could serve as impediments or frictional blocks towards movement as they may rub or grab onto the sides of whatever vessel or cavity they are being inserted into. Accordingly, to aid the catheter's insertion, the blister casing 112 may be shaped such that a fluid-filled blister will have an oval shape. To accomplish an oval blister shape, the blister casing 112 has an oval blister casing top 402 which when filled with fluid guides the shape of the final blister that is formed on the outside of the balloon casing 202 of the balloon catheter.

The oval blister casing top has a longer oval shaped side and a shorter oval shaped side. The longer oval shaped side may be aligned to run parallel to an alignment line of the insertion direction for the balloon catheter 404. Alignment of the longer side of the oval blister casing top 402 to the alignment line of the insertion direction for the balloon catheter 404 allows for easier insertion than if an oval shaped blister were aligned another way as it decreases the amount of blister casing 112 that would rub against a blood vessel upon insertion of the balloon catheter. In an example, one benefit of an oval blister casing top 402 is that it allows the transport of additional fluid without a linear increase in the amount of blister casing 112 used to encase the fluid on the balloon catheter. Accordingly, the oval blister casing top 402 may improve the fluid to blister casing ratio without increasing difficulty of insertion of the balloon catheter. Furthermore, once inserted, an oval blister inserted lengthwise along the alignment line of insertion would provide additional anchoring against rotation once inside a vessel when compared to a spherical blister casing top.

Figure 5:
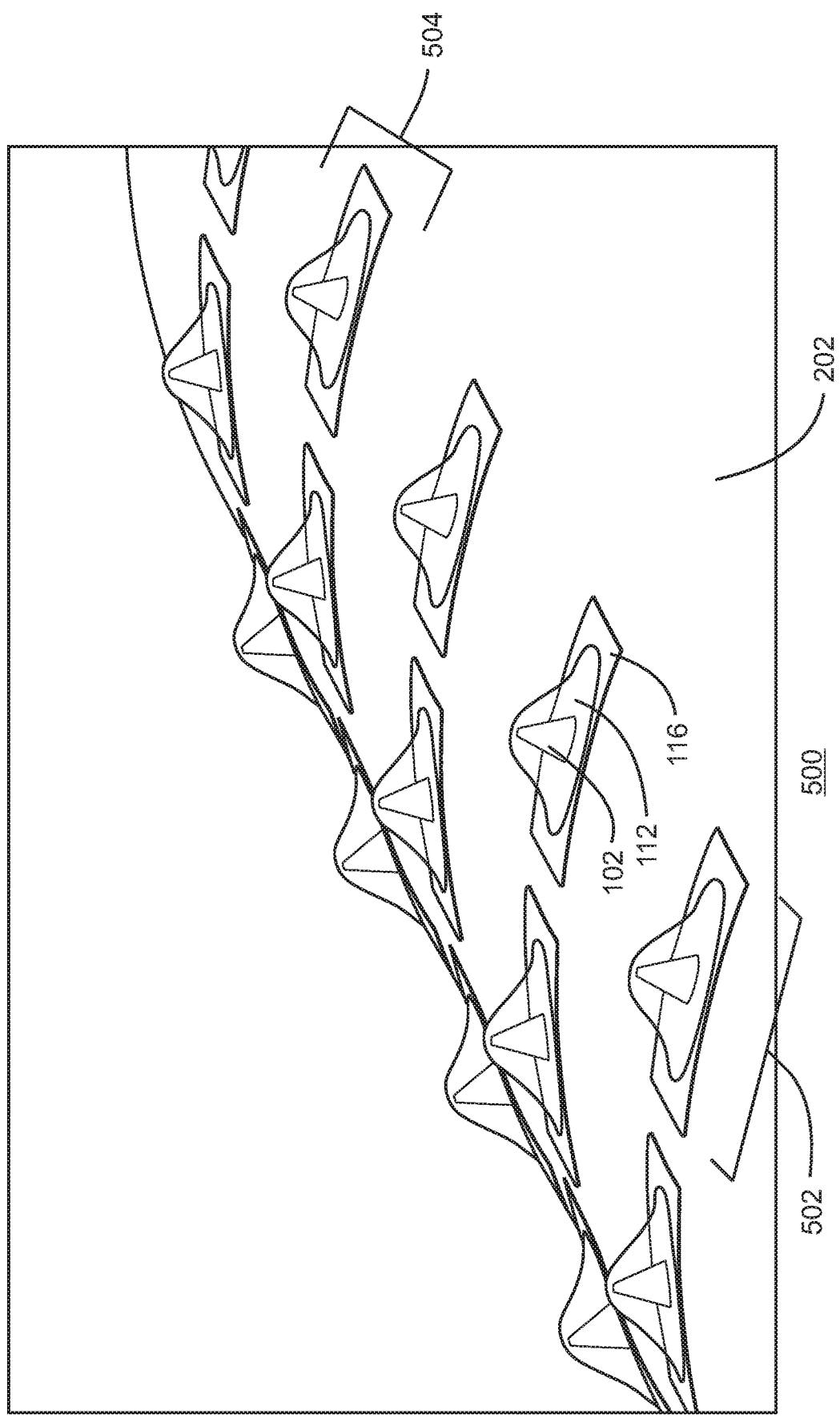
FIG. 5 is a diagram of rows of blisters in a blister configuration of a balloon catheter.

FIG. 5 is a diagram of rows of blisters 500 in a blister configuration of a balloon catheter. Like numbered items are as disclosed above. The blisters shown are attached to the balloon casing 202 in rows in various directions. A blister insertion direction row 502 runs parallel to the direction a balloon catheter is to be inserted. The alignment in a row or collection of rows in a line parallel to the insertion direction can ease insertion as it decreases the resistive friction of blisters. The collection of blisters into a row or rows rather than scattered to completely cover a circumference of a balloon casing reduces the profile of the balloon casing thus reducing the increased resistance a blister or number of blisters may have on an otherwise smooth balloon casing.

The balloon casing 202 may also include blisters attached and aligned in a blister rotation row 504. In an example, the blister rotation row 504 can be orthogonal to the blister insertion direction row 502. In an example, the blister rotation row 504 and blister insertion direction row 502 can be staggered to create a corkscrewing alignment of blisters along the balloon casing 202. The blister rotation row 504, when in aligned in an orthogonal rings or partial rings, where the blister rotation row 504 is orthogonal to the blister insertion direction row 502, decreases friction for a balloon casing rotating inside a vessel once the catheter is inserted. In an example, the ability to rotate a catheter inside of a vessel before inflation allows the spikes 102 and the fluid to be delivered directionally. In an example, if plaque is located on a left side of a vessel and not a top, bottom, or right side of the vessel, then it would be overmedicating to use a balloon catheter where spikes completely surround the balloon of the balloon catheter. Accordingly, the ability to rotate a balloon catheter inside of the vessel and also easing the rotation reduces potential unintended damage within the vessel.

Figure 6:
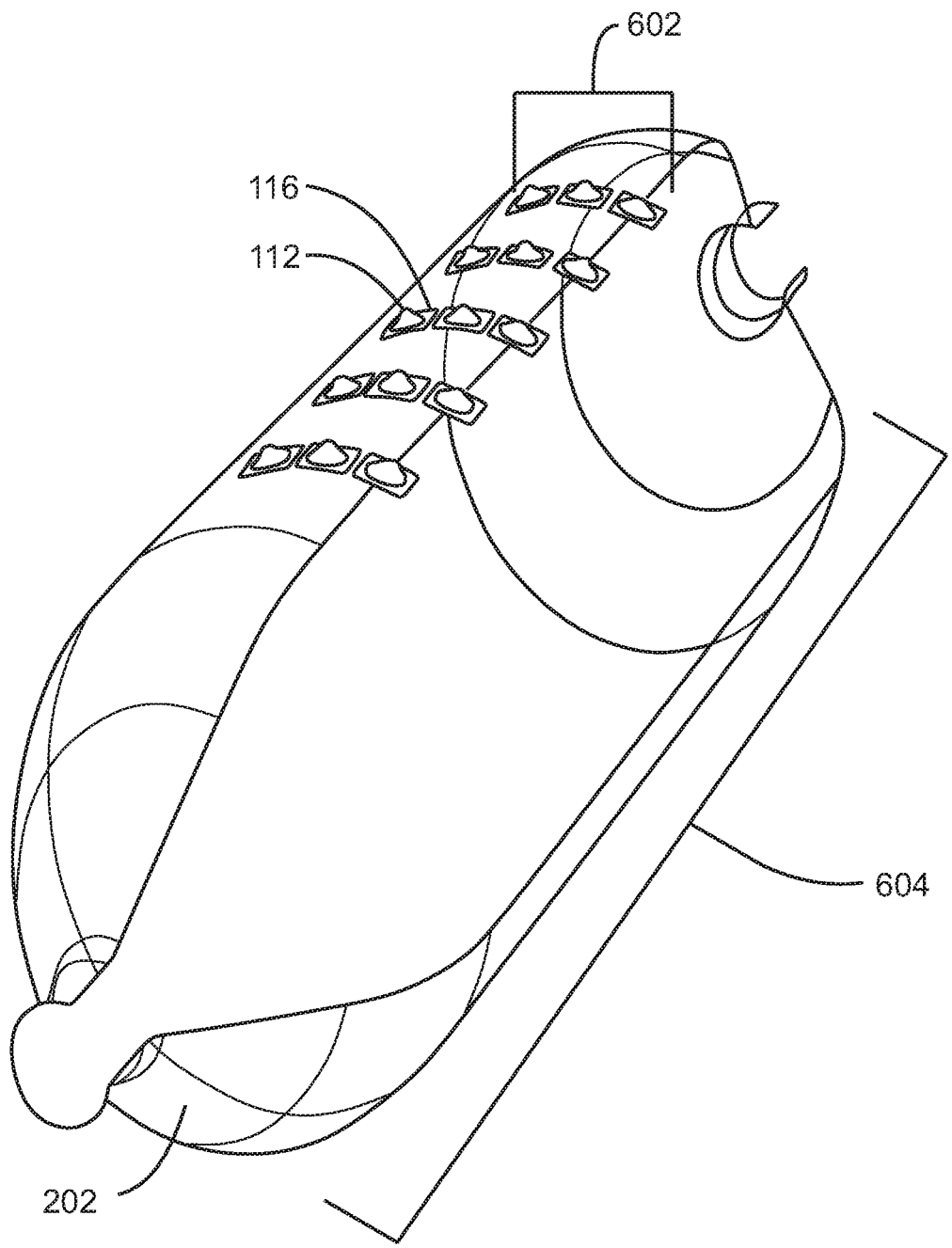
FIG. 6 is a diagram of a region of blisters in a blister configuration of a balloon catheter.

FIG. 6 is a diagram of a region of blisters 600 in a blister configuration of a balloon catheter. Like numbered items are as disclosed above. The balloon casing 202 is shown in an oval-like tube shape with ends that indicate an opening for tubing and a guidewire to pass through or into the balloon casing 202. The side view of the balloon casing in FIG. 6 is cut away to aid in showing the shape and hollowness of the balloon casing in a somewhat inflated state. As discussed above, when the balloon casing 202 is fully inflated, the blisters including the spikes inside the blisters are pressed outwards often through the blister casing 112 and into target areas.

As discussed above, blisters may ring the entire circumference of the balloon casing 202. Alternatively, the blisters may only cover a portion or part of the balloon casing 202. The blister region of balloon 602 indicates a side of the balloon casing 202 to be pointed towards and inflated into a target region of fluid and spike deployment. As discussed above, the use of spikes may be to anchor into an area or pierce plaque or a part of a vessel in order to eject medicine into a particular layer or region. The blister region of the balloon 602 allows the steering of the spikes and blister encased fluid towards a target area. The blister region of the balloon 602 is complimented by the blister-free region of the balloon 604. The blister-free region of the balloon 604 allows reduction in the number of blisters that are used for a balloon catheter thus reducing price for materials and balloon catheter assembly. Further, the blister-free region of the balloon 602 may be useful to ensure that a particular target region is not pierced by spikes that would have otherwise been present for fluid deployment. Protection of fragile areas of vessels while still being able to deploy the spikes and fluid ejection of the blister configuration of the balloon catheter increase the use cases for the balloon catheter to include those with thin, damaged, or weaker vessels.

Figure 7:
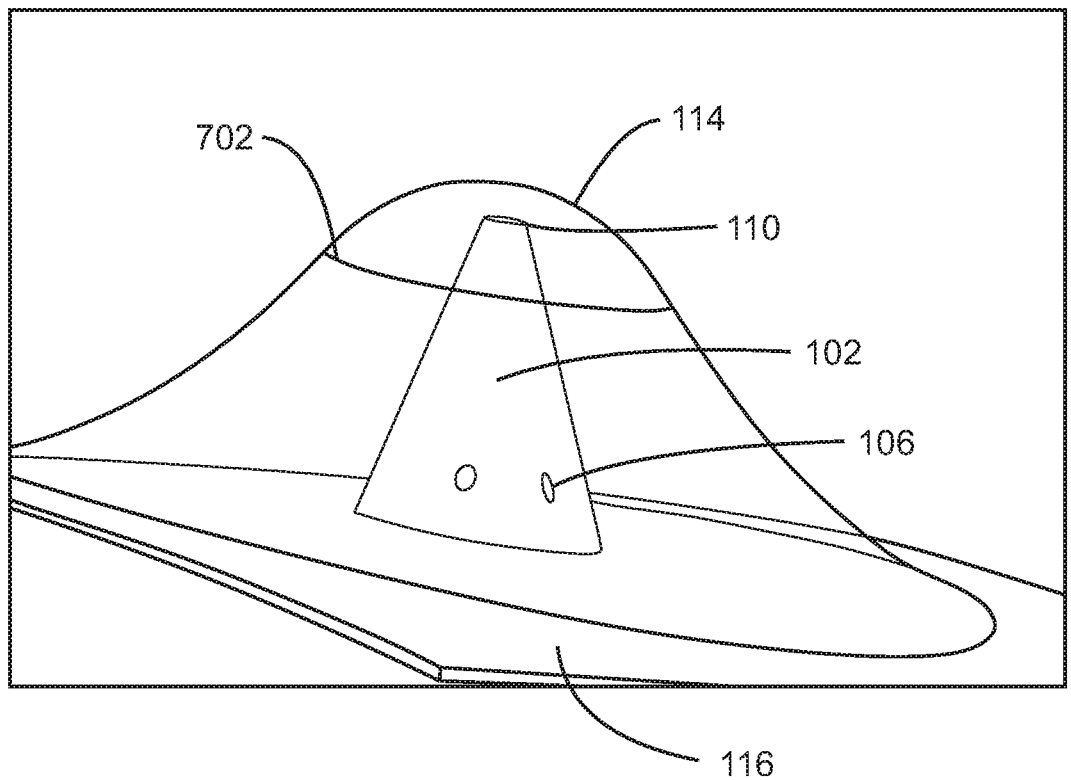
FIG. 7 is a diagram of a circular blister configuration of a balloon catheter.

FIG. 7 is a diagram of a circular blister configuration 700 of a balloon catheter. Like numbered items are as discussed above. As discussed above, the blister, and the blister casing 202, can take on a number of intended shapes when filled with fluid. In an example, the blister casing 202 may be a circular blister casing 702 in contrast with the oval blister casing shown in FIG. 4. While the oval blister casing may allow for increased volume of fluid without much increase in the area of a balloon catheter's insertion profiled, in contrast, the circular blister casing 702 reduces the resistance to the balloon catheter rotating in a direction orthogonal to the rotation direction. Accordingly, different balloon catheters may use one blister casing shape depending on the type of fluid that is to be deployed to the target area. As the blister casing in FIG. 7 shows a circular blister casing 702, the puncture region, is likely to match the shaping of the blister casing region.

Figure 8:
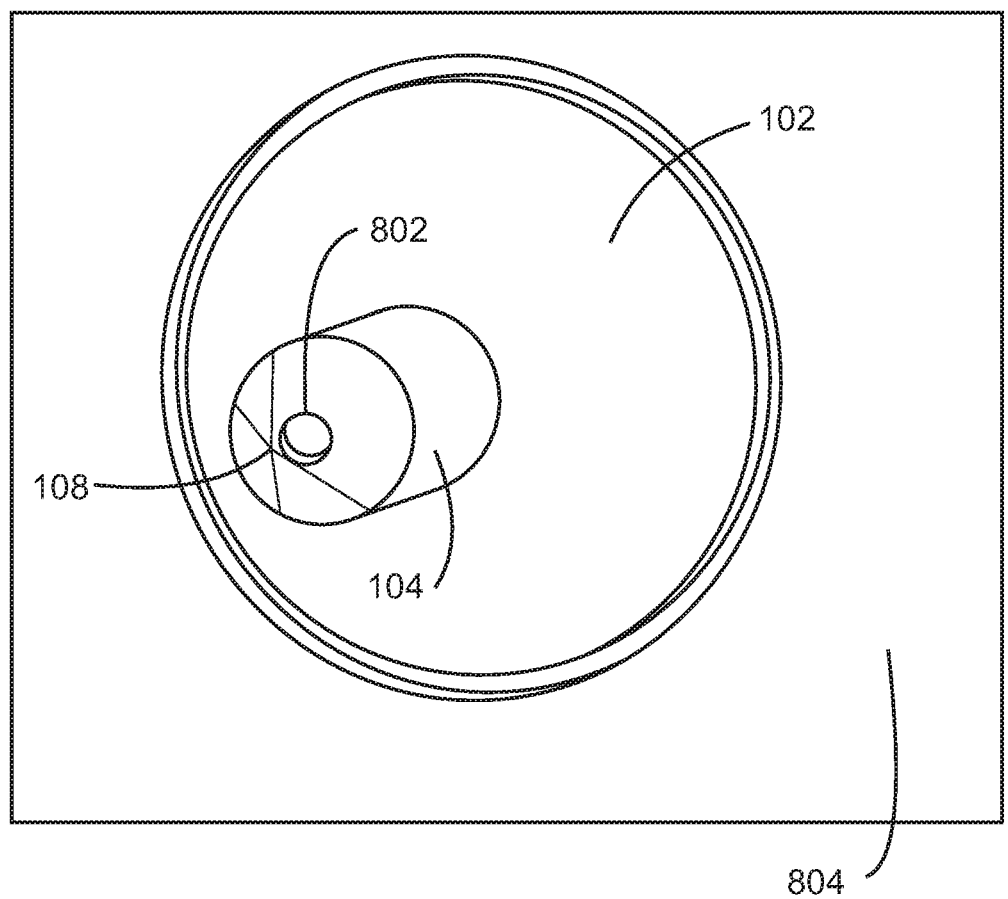
FIG. 8 is a diagram of a spike of a balloon catheter.

FIG. 8 is a diagram of a spike of a balloon catheter 800. Like numbered items are as disclosed above. As above, the spike 102 includes a shaft spike 104 and a spike pointed end 108. The spike 102 can also include an off-center spike outlet 802. The spike outlet may be off-center or on center in some examples, but the outlet is off-center for illustrative purposes in FIG. 8. Specifically, by locating the spike outlet off of the center of the spike pointed end 108, the spike 102 is allowed to have a solid singular point to aid in piercing a flexible layer as well as a plaque deposit or the layer of a vessel. The off-center spike outlet 802 while viewed from above may appear to be circular, however were the off-center spike outlet 802 to be viewed from the side, the location of the opening on the slanted surface of the spike pointed end 108 would elongate the circular opening into an oval. This elongation may allow for additional ability to guide the direction of the fluid ejected. Specifically, by using an off-center spike outlet 802 with an oval like opening in the spike pointed end 108, fluid may be ejected both out of the spike parallel with the spike shaft 104 and also may have a slight path deviation towards the greater size of opening of the off-center spike outlet 802. The increased flow in the direction of the off-center spike outlet could slightly adjust the flow of fluid away from the single spike point by an amount corresponding to how far way the off-center spike outlet 802 is from the center, or also how large the oval opening of the spike outlet may be.

Figure 11:
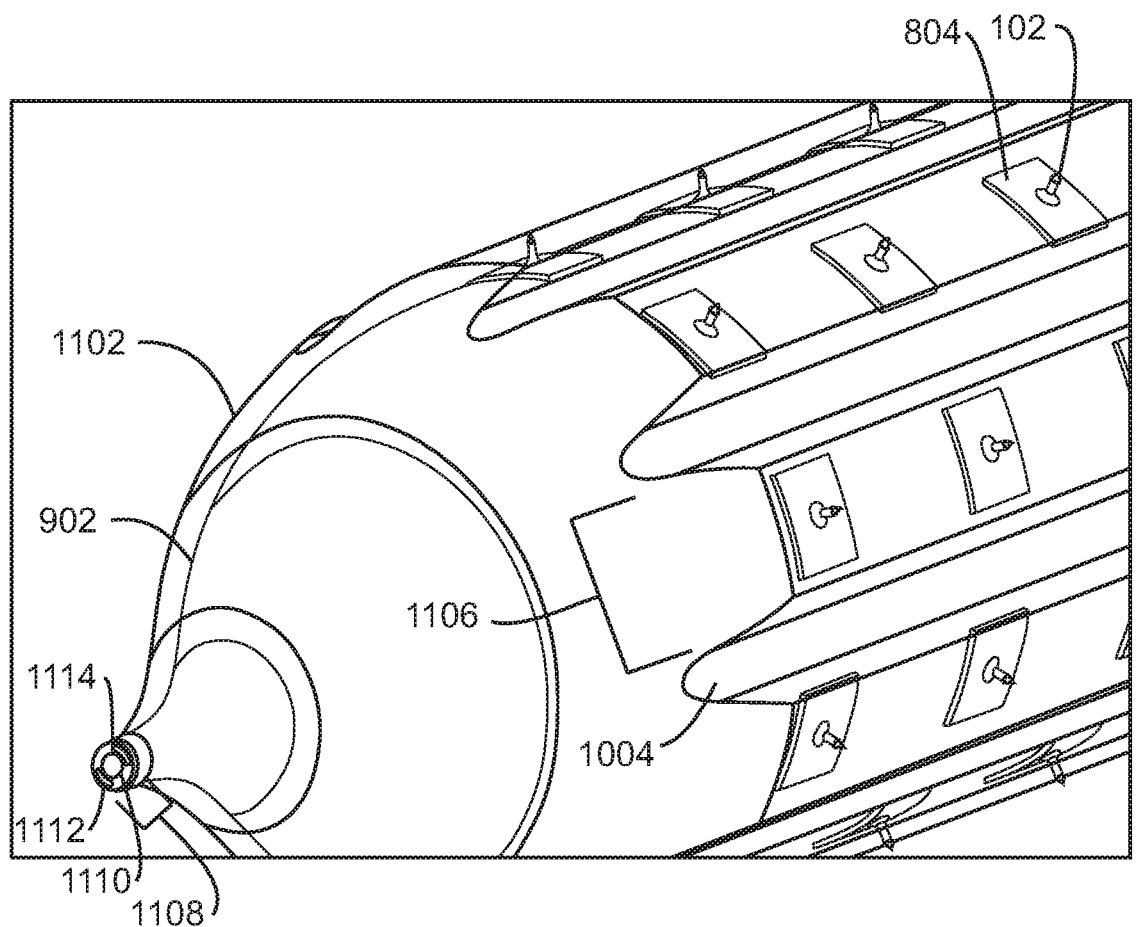
FIG. 11 is a diagram of a balloon catheter in a porcupine configuration.
Figure 18:
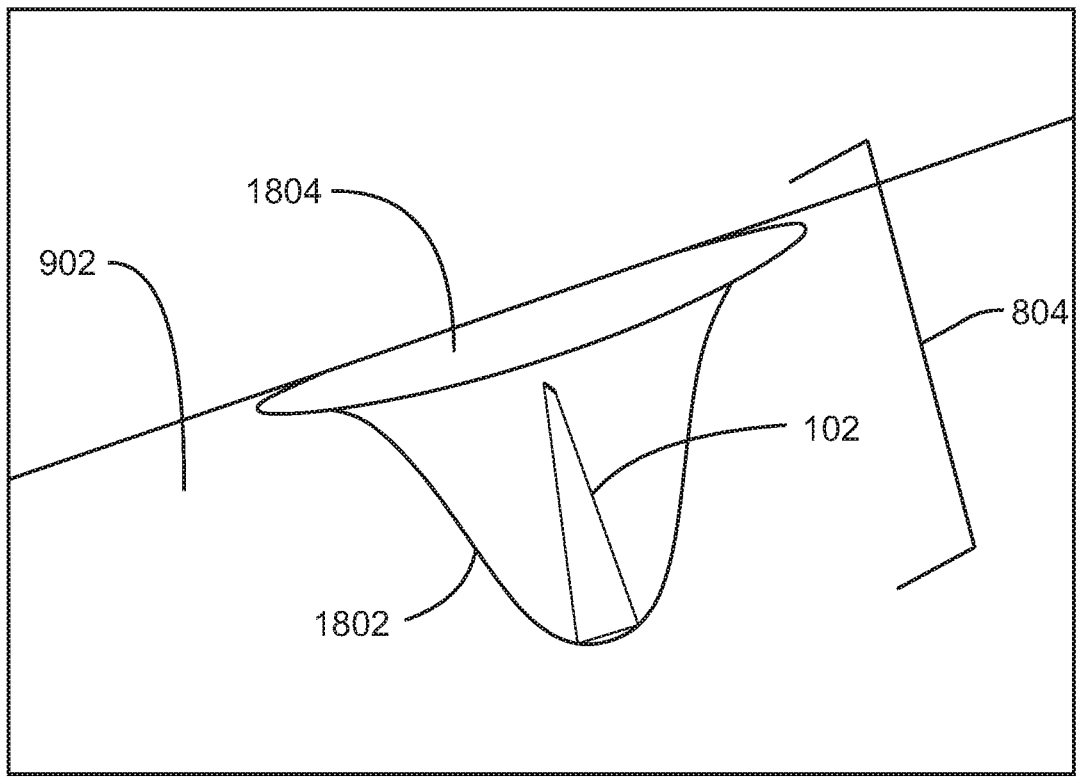
FIG. 18 is a diagram of a spike mounting platform for a balloon catheter using a reverse blister.

The spike 102 is shown mounted on the spike mounting platform 804. The spike mounting platform may be the same material as the balloon casing or may be a separate material. The spike 102 may be mounted to the spike mounting platform 804 through adhesive substance, through lamination, fusing, or other connection method. The spike mounting platform can be a more rigid or durable material compared to the blister casing or balloon casing to prevent the spike 102 from puncturing the spike mounting platform 804. In an example, the spike mounting platform may be more than a single material, and may itself be a blister or reverse blister or other configuration of nested balloons as shown in FIGS. 1, 11, and 18. The spike mounting platform 804 is shown with multiple heights as the spike 102 appears recessed into a slight depression of the spike mounting platform 804. In an example where the spike mounting platform is a single layer or piece of material, the recession may be built into the spike mounting platform to provide additional security of the spike 102 into the spike mounting platform 804. In an example, where the spike-mounting platform includes more than one layer or more than one material, the recessed layer to which the spike 102 is adhered may be a collapsed blister base layer and the upper region a punctured puncture region of a blister casing.

While FIG. 8 does not enumerate a spike inlet, at least one inlet may be present along the spike shaft 104. In another example, a spike inlet may be excluded from the spike shaft if the fluid is reaching the spike outlet from below the spike mounting platform such as the case with a reverse blister or other below casing fluid supply technique.

Figure 9:
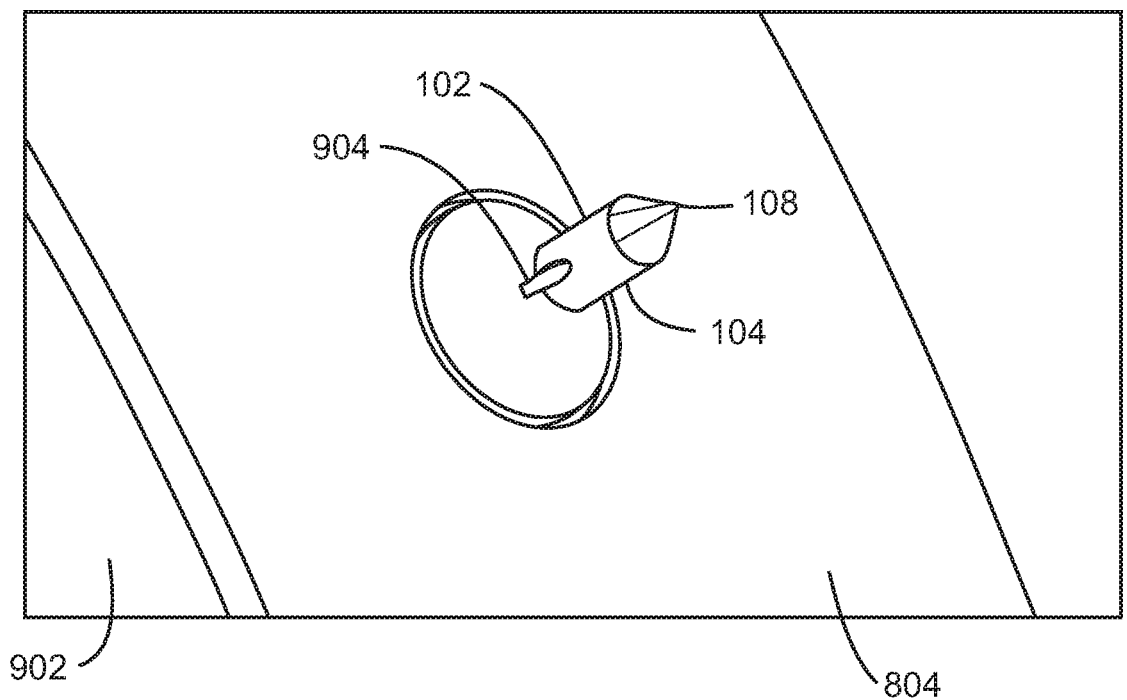
FIG. 9 is a side view of a spike of a balloon catheter.

FIG. 9 is a side view 900 of a spike of a balloon catheter. Like numbered items are as disclosed above. The balloon catheter may include a number of layers of balloon casings nested within one another to create additional channels and region for fluid flow and delivery. Accordingly, the spike mounting platform can be mounted on the inner balloon casing 902. As used herein, the inner balloon casing may be 'inner' in that the casing may be inside another layer of casing of a multi-layer balloon catheter. Accordingly, in this specific example, the inner casing and accompanying spike 102 may be inside another, larger, unseen casing of an overall balloon casing structure. The inner balloon casing may include a spike 102 mounted to a spike mounting platform 804. In an example, the inner balloon casing 902 can be the same material as the spike mounting platform 804 or a different material with the spike mounting platform 804 affixed, laminated, mounted, or otherwise attached to the inner balloon casing 902.

The spike 102 may include a puncture-direction-lengthened spike inlet 904. The spike 102 has a spike shaft that 104 that aligns itself in a puncture direction that is relatively orthogonal to the insertion direction of a balloon catheter. The puncture direction run approximately along the line parallel with the spike shaft 104 towards the spike pointed end 108. Lengthening the spike inlet can allow increased rate of intake of fluids as well as altering the direction of intake of fluids so that any fluid movement is channeled towards a puncturing direction, or the spike pointed end 108. While the puncture-direction-lengthened spike inlet may appear roughly oval or rectangular from the side, the inlet may appear circular or square when viewed form a spike pointed end 108.

Figure 10:
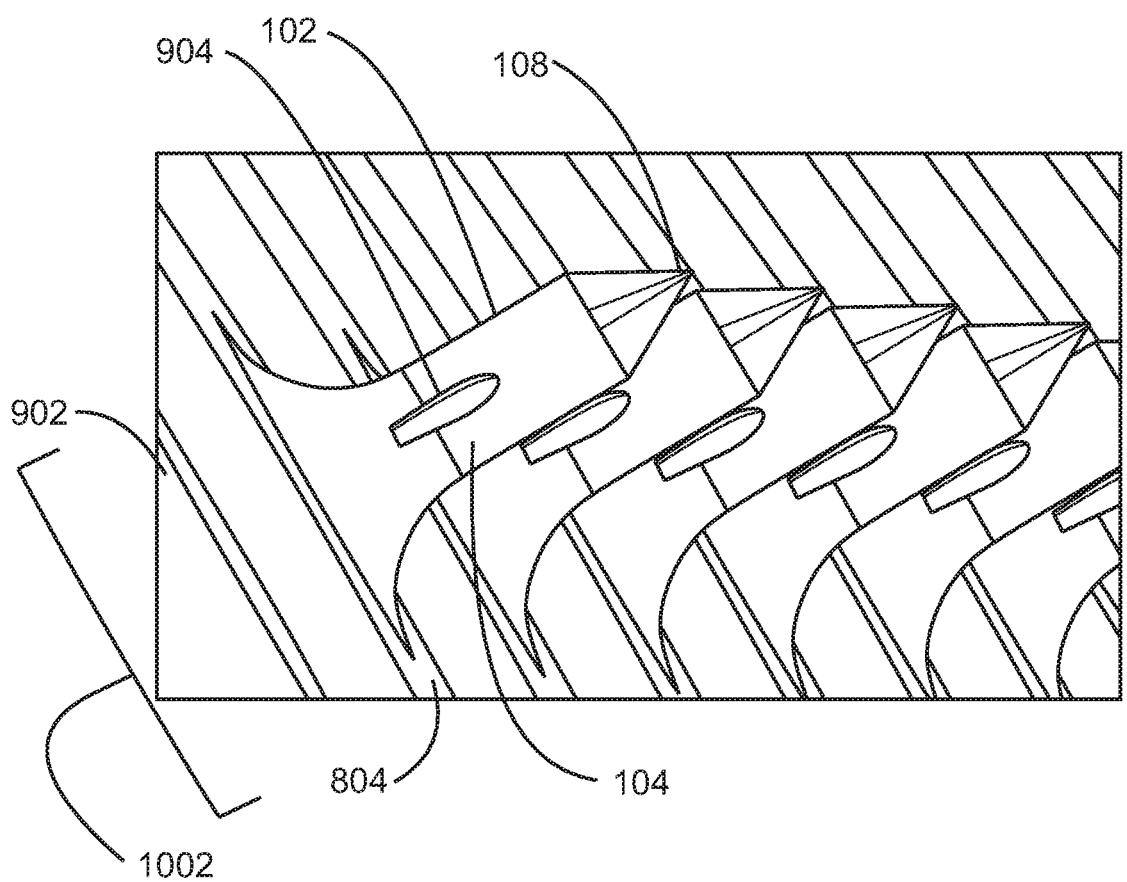
FIG. 10 is a diagram of a row of spikes in a porcupine configuration of a balloon catheter.

FIG. 10 is a diagram of a row of spikes in a porcupine configuration 1000 of a balloon catheter. Like numbered items are as disclosed above. The catheter insertion direction row 1002 shows that a number of spikes 102 may be aligned along an inner balloon casing 902 to create a single row of spikes that can be slid into a vessel rather than a random placement that could increase surface area of the balloon catheter when being inserted into the vessel thus obstructing insertion. Further, by grouping the spikes 102 into a catheter insertion direction row 1002, this allows areas of the inner balloon casing 902 to be free of spikes 102 and spike mounting platforms 804 thereby creating space for the inner balloon casing to be connected or fused other casings, layers, catheter tubing connectors, and increasing ability to expand and contract without accounting for other more rigid objects such as spikes 102.

FIG. 11 is a diagram of a balloon catheter in a porcupine configuration 1100. Like numbered items are as disclosed above. This view shows a zoomed out view of a balloon catheter in a porcupine configuration 1100. The outer balloon casing 1102 is shown enclosing the spikes 102, spike mounting platform 804, and inner balloon casing 902. The spikes 102 are shown pushing through the outer balloon casing indicating that this balloon catheter is in an inflated position. If the balloon catheter were in a deflated position, then the spikes would not be puncturing the outer balloon casing 1102. In an example, when a balloon catheter has not been inflated, both the inner balloon casing 902 and the outer balloon casing 1102 are both flexible and separate layers and the outer balloon casing 1102 is not punctured by spikes 102. Then upon inflation, the inner balloon casing 902 expands pushing the outer balloon casing 1102 outward along with it. During inflation of the balloon catheter, specifically the inner balloon casing 902, the outer balloon casing 1102 may slow or stop expanding due to being be less expandable than the inner balloon casing 902 or due to impedance by a vessel wall, plaque deposits, or the like. In response to the slowed or stopped expansion of the outer balloon casing 1102 and the continued expansion of the inner balloon casing 902, the spikes 102 mounted on the spike mounting platform 804 of the inner balloon casing 902 may puncture and push through the outer balloon casing 1102. The puncture and pushing through of spikes through the outer balloon casing 1102 may allow the spikes to eject fluid towards a target area such as plaque deposits, a vessel wall, or other suitable target area of a catheter delivering fluids to a specified region.

As disclosed above with respect to the rows of spikes, the spikes 102 are aligned in a row parallel with the insertion direction. This allows areas of spikes 102 and areas free of spikes along the inner balloon casing 902. The outer balloon casing 1102 and the inner balloon casing 902 can be fused together using heating and cooling of the two casings, adhesive substances, physical interlacing, or other suitable attachment means. The regions of attachment between the outer balloon casing 1102 and the inner balloon casing 902 can be called the balloon casing layer attachment 1104. The creation of one or more balloon casing layer attachment 1104 may correspond to the two sides of a row of spikes 102 mounted on the inner balloon casing 902. By attaching the outer balloon casing 1102 to the inner balloon casing 1102, a fluid flow channel 1106 is formed. The fluid flow channel 1106 allows fluid to flow around and to the spikes 102 in the porcupine configuration. In an example, the balloon catheter may not have fluid stored in blisters of the spike 102 and the fluid will be instead supplies from the region between the inner balloon casing 902 and the outer balloon casing 1102. The creation of a fluid flow channel 1106 can direct the flow of fluid from a catheter tubing connector 1108 toward the spikes 102. The catheter tubing connector may be made of rigid plastic, metal, or other suitable material for channeling fluids and resisting damage due to contact with other hard materials.

Once the fluid can access the spikes 102 and the spikes have punctured the outer balloon casing 1102, the fluid can pass through the spikes 102 towards a target area. By creating a fluid flow channel 1106 and a balloon casing attachment 1104, the flexibility of the outer balloon casing is limited at the places of casing attachment. The inner balloon casing 902 may expand further into the fluid flow channel 1106 upon initial inflation in order to puncture the outer balloon casing 1102.

The catheter tubing connector 1108 allows catheter tubing to connect, guide, and provide fluid and inflation to the balloon catheter. The catheter tubing connector 1108 includes a catheter guide wire opening 1110 through the core of the catheter tubing connector 1108. The catheter guide wire opening 1110 is an opening that a guide wire may be inserted through. When a balloon catheter is inserted into a vessel, it can be following a guide wire already inserted or be pushed by a guidewire towards a target destination within the vessel. The catheter guide wire opening 1110 is located on the catheter tubing connector 1108 to provide a sturdy durable contact point for the guide wire to avoid direct contact with the flexible balloon casings that might cause damage through pinching or friction.

The catheter tubing connector 1108 includes a tubing-to-balloon fluid port 1112. The tubing-to-balloon fluid port 1112 allows fluid to be pumped into the region between the inner balloon casing 902 and the outer balloon casing 1102. As discussed above, the fluid may be an inert saline solution used to break up a plaque deposit. The fluid may also be indicator, medicine, a genetic, a biological agent that alters the function and structure of the vessel, or specific vitamins, nutrients, or other chemicals that provide the vessel a localized delivery of these agents. The catheter tubing connector 1108 also includes a tubing-to-balloon inflation port 1114. The tubing-to-balloon inflation port 1114 allows fluid such as a liquid or air to be pushed into the region inside the inner balloon casing 902. As the inner balloon casing 902 is inflated by fluid flowing through the tubing-to-balloon inflation port 1114, the inner balloon casing 902 expands pushing both the spike mounting platform 804 and the spike 102 outward. As the inner balloon casing 902 expands the outer balloon casing 1102 may also expand.

As disclosed above, the outer balloon casing 1102 may be flexible although less expandable than the inner balloon casing 902. Accordingly, the outer balloon casing 1102 may stop or slow expanding while the inner balloon casing 902 continues expansion. The continued expansion of the inner balloon casing 902 presses the spike 102 through the outer balloon casing 1102. When the spike 102 punctures the outer balloon casing, the spike 102 may act as a conduit for fluid from the fluid flow channel 1106 to the target area.

In an example, the fluid flow channel 1106 and the region between the inner balloon casing 902 and outer balloon casing 1102 do not hold fluid prior to inflation. In an example, the fluid flow channel 1106 and the region between the inner balloon casing 902 and outer balloon casing 1102 have some fluid hold fluid prior to inflation. In an example, the fluid flow channel 1106 and the region between the inner balloon casing 902 and outer balloon casing 1102 do not hold fluid prior to puncture of the spike 102 through the outer balloon casing 1102. In an example, the fluid flow channel 1106 and the region between the inner balloon casing 902 and outer balloon casing 1102 are filled with fluid through the tubing-to-balloon fluid port 1112 after the inner balloon casing 902 has been inflated. In an example, the fluid flow channel 1106 and the region between the inner balloon casing 902 and outer balloon casing 1102 are filled with fluid through the tubing-to-balloon fluid port 1112 after the spike 102 punctures the outer balloon casing 1102. When the spike 102 punctures the outer balloon casing 1102 the outlet of the spike 102 may be outside the outer balloon casing 1102 while the inlet of the spike 102 along the spike shaft is located in the fluid flow channel 1106 between the inner balloon casing 902 and the outer balloon casing 1102. The location of the spike inlet and spike outlet allows the spike to be a conduit for fluid flowing from inside the fluid flow channel 1106 through the spike 102 and towards a target area.

Figure 12:
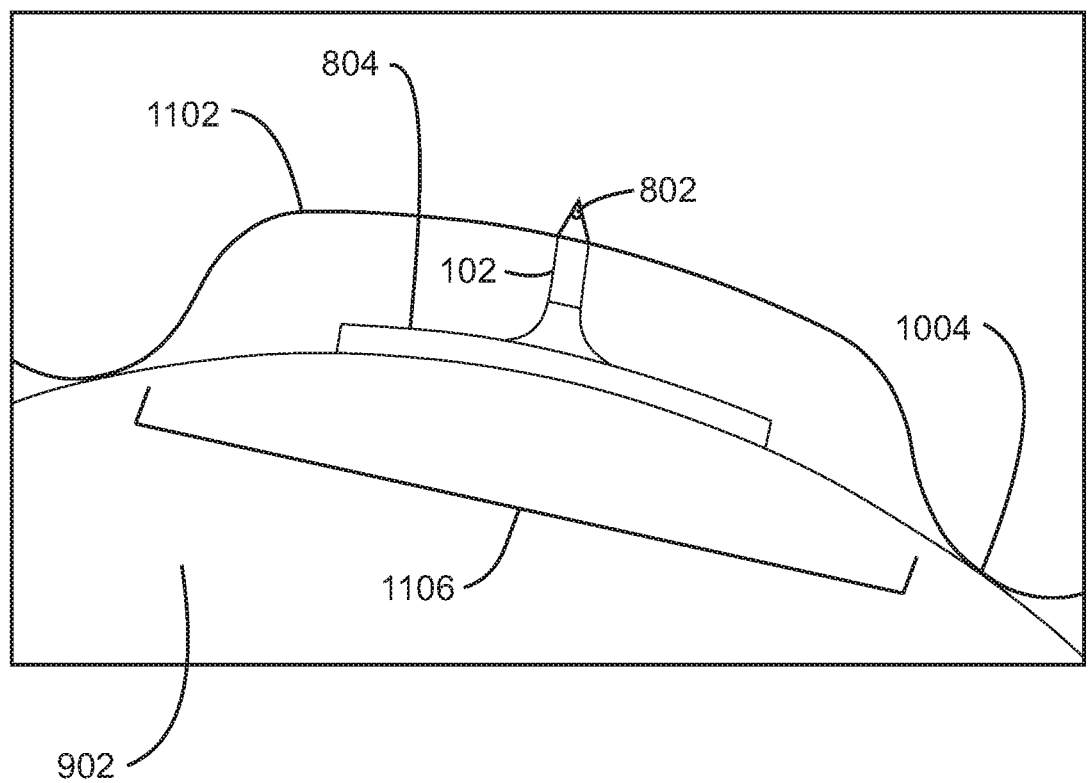
FIG. 12 is a side view of a fluid flow channel of a balloon catheter.

FIG. 12 is a side view 1200 of a fluid flow channel 1106 of a balloon catheter. Like numbered items are as disclosed above. FIG. 12 largely shows the same items as disclosed in FIG. 11 with a varied point of view to show in greater detail one aspect of the balloon catheter. As shown, the fluid flow channel 1106 is formed through the separation of the inner balloon casing 902 and the outer balloon casing 1102 as well as the balloon casing later attachment 1104 on either side of the fluid flow channel 1106. The spike 102 shown has punctured the outer balloon casing 1102. Prior to inflation or puncture of the outer balloon casing 1102, the spike 102 may be hosed between the outer balloon casing 1102 and the inner balloon casing 902 and the outer balloon casing may be un-punctured until sufficient inflation of the inner balloon casing 902. The view of FIG. 12 illustrates a side view of the fluid flow channel 1106 where fluid may pass between the two layers of inner and outer casing and to the spike 102. As disclosed above, when the spike 102 has punctured the outer balloon casing 1102, fluid from the fluid flow channel 1106 can flow into an inlet of the spike 102 through the spike shaft and out the spike outlet, which is shown in FIG. 12 as an off-center spike outlet 802.

Figure 13:
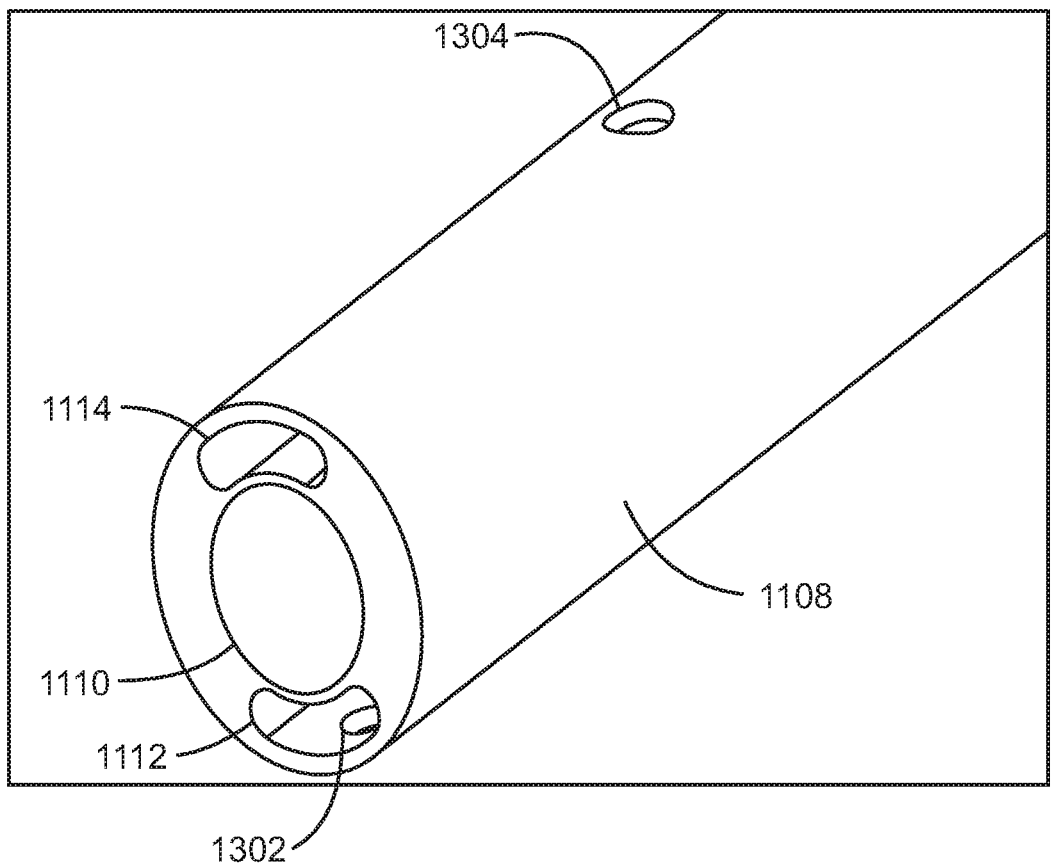
FIG. 13 is a diagram of a catheter tubing connector.

FIG. 13 is a diagram of a catheter tubing connector 1300. Like numbered items are as disclosed above. The catheter tubing connector 1108 is shown without tubing or an inner or outer casing attached. The catheter tubing connector 1108 includes an opening to space between inner and outer balloon casing for fluid 1302 that acts as an opening in the catheter tubing connector 1108 for fluid to flow from the tubing-to-balloon fluid port into the space between the inner and outer casing of a balloon. The catheter tubing connector 1108 includes an opening to inflate inner balloon casing 1304 that allows an inflation fluid such as air or saline or other inflation means to pass through the tubing-to-balloon inflation port 1114, through the catheter tubing connector 1108 and into the inner balloon casing 902.

Figure 14:
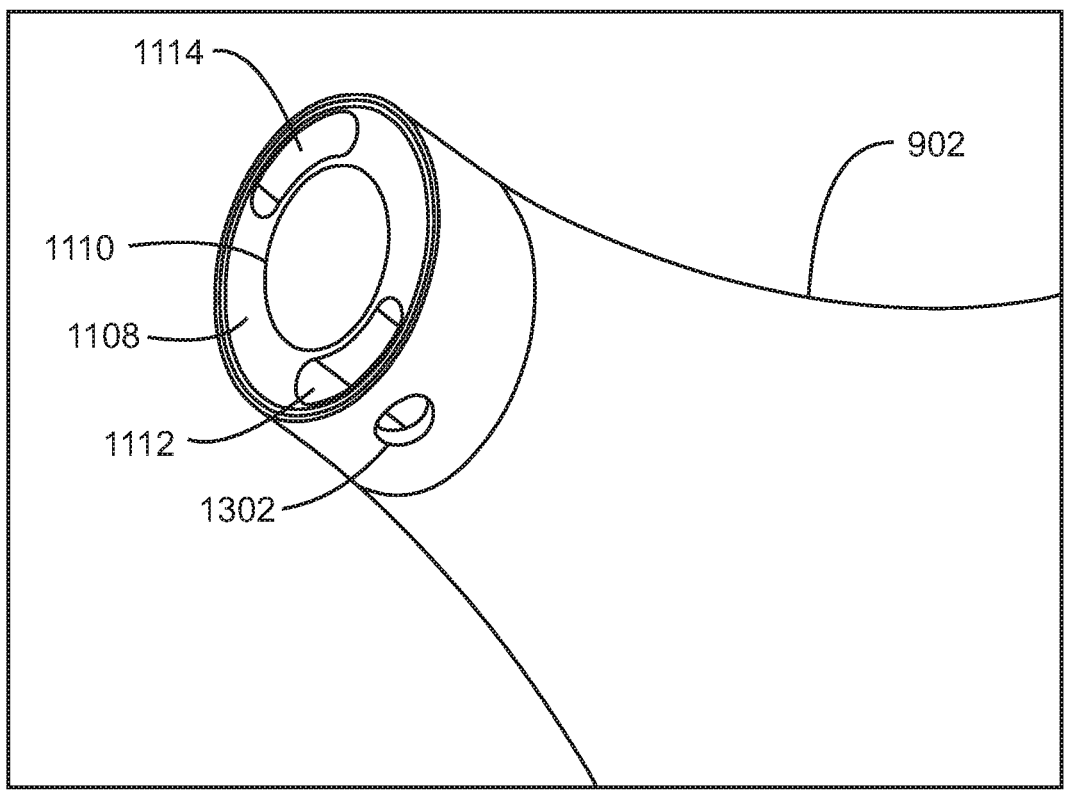
FIG. 14 is a diagram of a catheter tubing connector with an attached inner balloon casing.

FIG. 14 is a diagram of a catheter tubing connector with an attached inner balloon casing 1400. Like numbered items are as disclosed above. The inner balloon casing 902 is shown pulled over and onto the catheter tubing connector 1108. When the inner balloon casing 902 is pulled onto the catheter tubing connector 1108, the opening to inflate inner balloon casing 1304 is covered by the inner balloon casing 902 such that the inner balloon casing 902 can be inflated through the tubing-to-balloon inflation port 1114.

In an example, the catheter tubing connector 1108 includes an inner balloon casing clamp 1402 to slide over the inner balloon casing 902 around the edge of the catheter tubing connector 1108. The inner balloon casing clamp 1402 as well as the inner balloon casing 902 can include a hole in the location of the opening to space between inner and outer balloon casing for fluid 1302. The hole in this location will allow fluid to flow through the tubing-to-balloon fluid port 1112 and out of the opening to space between inner and outer balloon casing for fluid 1302 and eventually into a fluid flow channel 1106. In another example, the catheter tubing connector 1108 may avoid the use of an inner balloon casing clamp 1402 and instead rely on the elastic force of the inner balloon casing 902 to grip onto the end of the catheter tubing connector 1108.

Figure 15:
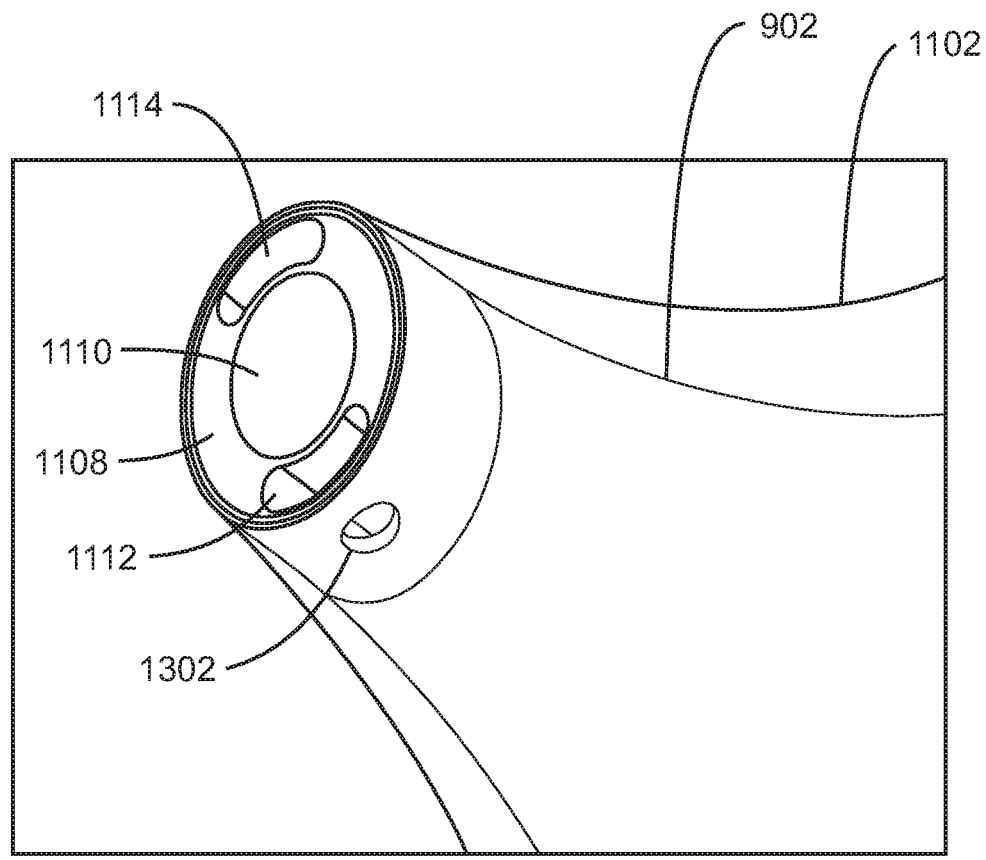
FIG. 15 is a diagram of a catheter tubing connector with an attached inner balloon casing and an attached outer balloon casing.

FIG. 15 is a diagram of a catheter tubing connector with an attached inner balloon casing and an attached outer balloon casing 1500. Like numbered items are as described above. The outer balloon casing 1102 may also be attached to the catheter tubing connector 1108 over the inner balloon casing 902 as well as the opening to space between inner and outer balloon casing for fluid 1302. The location of the attached outer balloon casing 1102 allows fluid to enter the tubing-to-balloon fluid port 1112 and out of the opening to space between inner and outer balloon casing for fluid 1302 and eventually into a fluid flow channel 1106. The outer balloon casing 1102 may be attached to the catheter tubing connector 1108 through the elastic force of the flexible outer balloon casing 1102 gripping the catheter tubing connector 1108. In an example, the outer balloon casing 1102 can be attached to the catheter tubing connector 1108 by being tucked inside the inner balloon casing clamp 1402. In an example, the outer balloon casing 1102 may have a casing clamp independent of the inner balloon casing clamp 1402.

Figure 16:
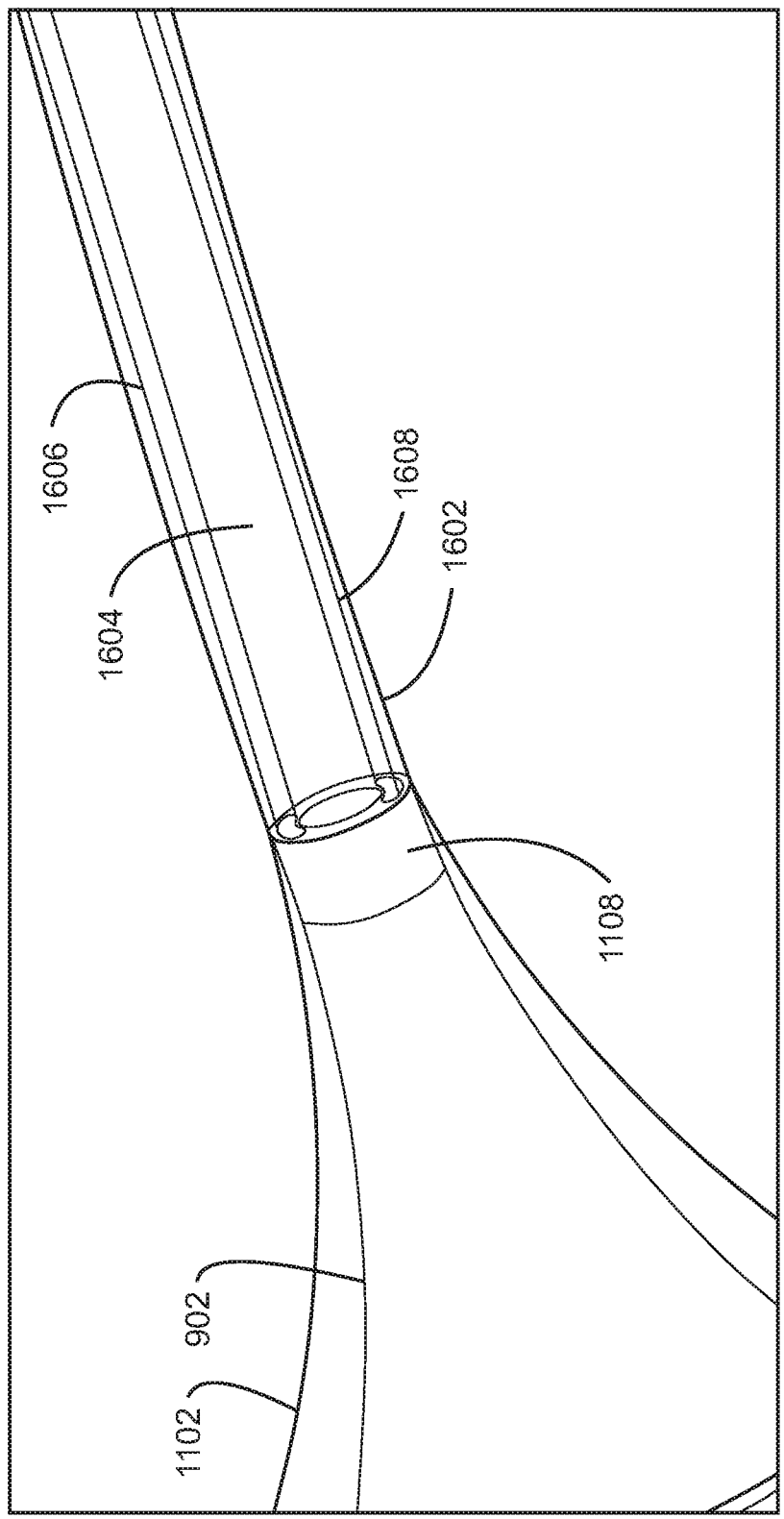
FIG. 16 is a diagram of catheter tubing connecting to the catheter tubing connector.

FIG. 16 is a diagram of catheter tubing connecting to the catheter tubing connector 1600. Like numbered items are as disclosed above. The catheter tubing 1602 is connected to the catheter tubing connector 1108. This allows the flow of fluid through the catheter tubing into the balloon catheter for inflation and fluid delivery. The catheter tubing 1602 includes a tubing guide wire channel 1604 that provides a space for a catheter guide wire to be passed through as the balloon catheter via the catheter guide wire opening 1110 and the catheter tubing 1602 as the both the tubing and balloon are pushed along a guide wire into a vessel. The catheter tubing 1602 includes a tubing inflation channel 1606 that connects to the tubing-to-balloon inflation port 1114 of the catheter tubing connector 1108 to allow inflation fluid to flow into the inner balloon casing 902. The catheter tubing 1602 includes a tubing fluid channel 1608 that connects to the tubing-to-balloon fluid port 1112 of the catheter tubing connector 1108 to allow fluid to flow into the space between the inner balloon casing 902 and the outer balloon casing 1102.

Figure 17:
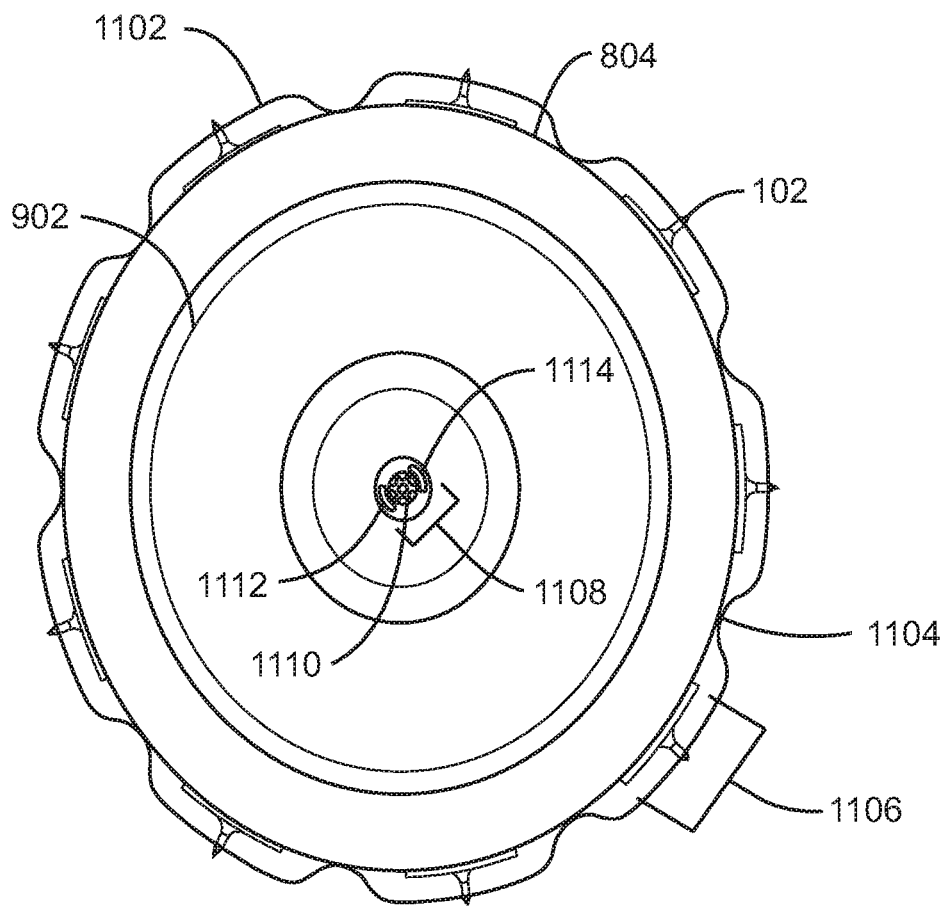
FIG. 17 is a side view of a balloon catheter in a porcupine configuration.

FIG. 17 is a side view of a balloon catheter in a porcupine configuration 1700. Like numbered items are as disclosed above. FIG. 17 shows the balloon catheter from the side in a view that is parallel to an insertion direction. The spikes 102 are shown puncturing the outer balloon casing 1102. In this example, the spikes 102 are shown wrapping around the circumference of the balloon catheter. In an example, the spikes 102 may cover a portion of the circumference of the balloon catheter so that when inflated, the spikes 102 puncture a balloon outer casing 1102 at a specific area. The portion of the balloon catheter circumference cover by spikes 102 can be limited to a single one-half side of the balloon catheter or any other fractional portion of the balloon catheter circumference.

FIG. 18 is a diagram of a spike mounting platform for a balloon catheter using a reverse blister 1800. Like numbered items are as described above. The reverse blister casing 1802 and the reverse blister puncture region 1804 may be part of a spike mounting platform 804. The reverse blister may be an enclosed region including a spike 102 and fluid that may pass through the spike 102 in response to the spike puncturing the reverse blister puncture region 1804. As used herein, the term enclosed may include generally encased and need not be a perfect seal of materials or full encapsulation. The fluid may be an indicator to aid in identifying the location of a spike 102 in a vessel. For example, indicator ejected into a vessel may be detectable through ultrasonic, laser, fluoroscopic or other x-ray scanning technology such as computerized axial tomography. The fluid encased in the reverse blister may also be any other kind of fluid that a spike 102 be used to eject towards a target area.

The reverse blister casing 1802 may be fused to the reverse blister puncture region 1804 which itself may be fused to the balloon casing. In an example, the reverse blister may be attached to an inner balloon casing 902 of a porcupine balloon catheter configuration as shown in FIG. 11. If the reverse blister is attached to the inner balloon casing 902 of a balloon catheter in porcupine configuration, then the spike 102 would be pushed through the reverse blister puncture region 1804 by the inflating of the inner balloon casing 902. After puncturing the reverse blister puncture region 1804 the spike may still be located between the inner balloon casing 902 and the outer balloon casing 1102. Further inflation may allow the spike 102 to puncture not only the reverse blister puncture region 1804 but additionally the outer balloon casing 1102 in order to access the target area such as a plaque deposit or a particular layer of a vessel. The reverse blister puncture region 1804 may be part of the inner balloon casing 902 or a separate material. As the reverse blister puncture region 1804 may be attached to balloon casing that expands or contracts based on inflation level, the reverse blister puncture region may be flexible material as well as thin enough to be punctured by the spike 102. In an example, the stretching of the reverse blister puncture region 1804 may also pull the reverse blister casing 1802 tighter and thus pull the spike 102 towards and eventually through the reverse blister puncture region 1804. In an example, the reverse blister casing 1802 may be pushed towards the reverse blister puncture region 1804 based on a pressure inside the inner balloon casing 902.

In an example, the reverse blister may be installed on a balloon casing 202 for a balloon catheter in a blister configuration as seen in FIG. 6. The use of a reverse blister on a balloon casing 202 in a blister configuration would eliminate the bumps on the outside of the balloon catheter and ease the ability of the balloon catheter to be inserted into a vessel.

Figure 19:
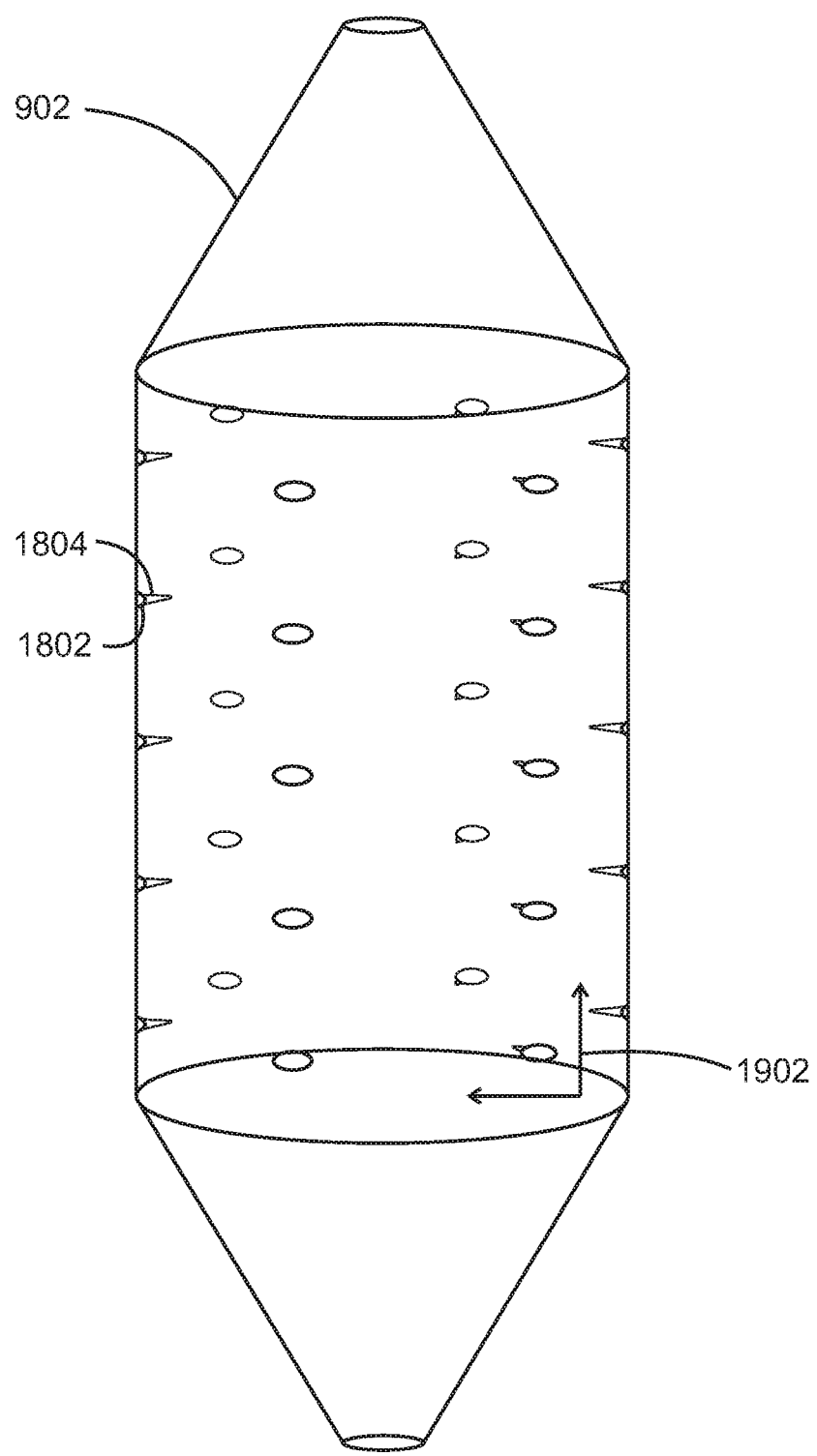
FIG. 19 is a diagram of a balloon catheter with direction balloon markings.

FIG. 19 is a diagram of a balloon catheter with direction balloon markings 1900. Like numbered items are as disclosed above. The balloon casing may be an inner balloon casing 902 and may include reverse blisters using reverse blister casing 1802 and reverse blister puncture regions 1804. As disclosed above, the balloon casing for use with reverse blister casings may also be the balloon casing 202 shown in FIG. 2 where only a single balloon casing layer is used.

The balloon casing may include directional balloon markings 1902. These directional balloon markings may be present on the outside or the inside of the balloon casing. The directional balloon markings 1902 may indicate an orientation of the balloon catheter in three directions. The directional balloon markings 1902 may be physical patterns etched into the balloon casing. In an example, the directional balloon markings 1902 may be indicator applied to the balloon casing that are viewable through the use of infrared, x-ray, or other medical imaging technologies. The orientation of the balloon can be useful for determining when to inflate the balloon. As discussed above, the inflation of the balloon can lead to the puncturing of at least one flexible casing layer such as the reverse blister puncture region 1804, the puncture region 114 in a blister configuration, or the outer balloon casing 1102 in a porcupine configuration of a balloon catheter. In an example, where the balloon includes both a reverse blister configuration and an inner and outer balloon casing, the spike 102 may need to puncture more than one flexible layer of casing material.

As the inflation of the balloon can lead to the deployment of spikes and the puncturing of a balloon casing, the location of the balloon within a vessel may be useful for determining if the balloon, once inflated, will be located appropriately with respect to a plaque deposit that is targeted. Further, the positioning may be important for confirmation of location before inflation if the spikes 102 are to be inflated into the layers of a vessel. In an example, the spikes 102 are located on a portion of the circumference of the balloon rather than the entire circumference, where the location and rotational position of the balloon catheter can matter in more than one dimension. For balloons with partial spike coverage, the orientation and location of the balloon may be relevant if a target area, such as a plaque deposit is located on one side of a vessel. In this example, based on the directional balloon markings 1902, the balloon may be rotated in place inside the vessel until the directional balloon markings 1902 indicate that the spikes 102 will deploy in the correct direction and area.

Figure 20:
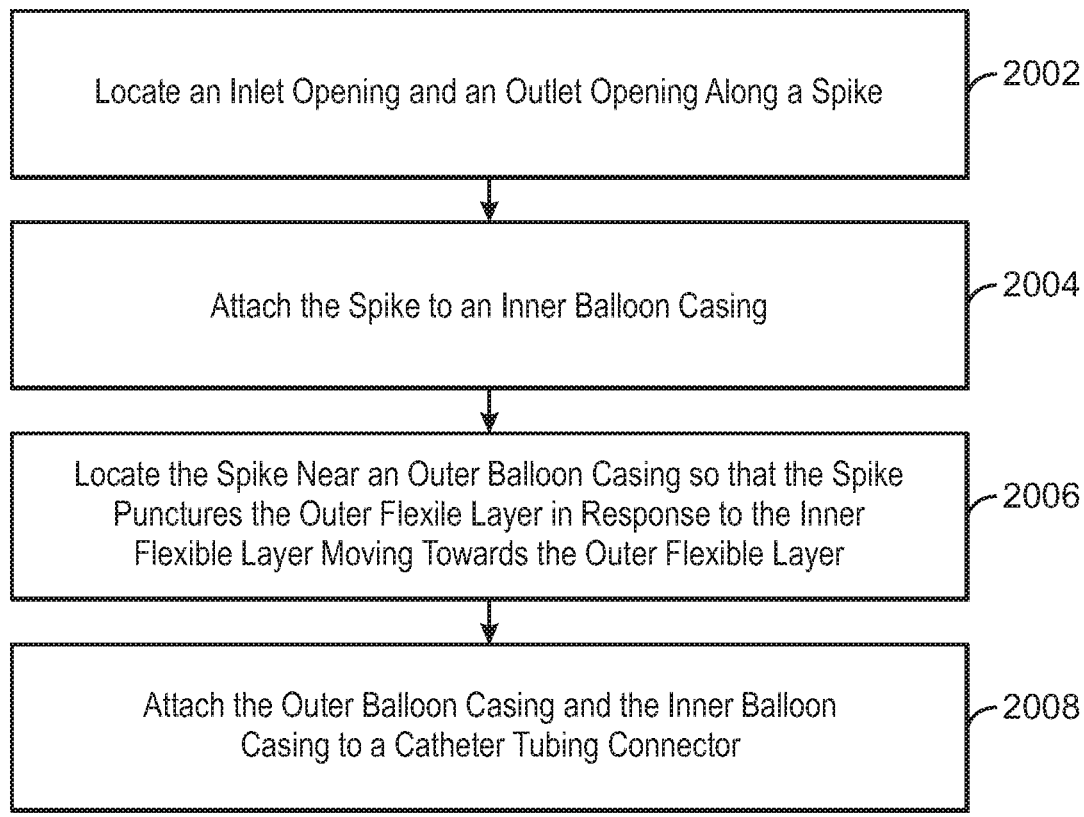
FIG. 20 is a process flow diagram showing an example method for manufacturing a balloon catheter device.

FIG. 20 is a process flow diagram showing an example method 2000 for manufacturing a balloon catheter device. At block 2002, the method includes locating an inlet opening and an outlet opening along a spike including a base end and a pointed end, an inlet opening located along the shaft of the spike between the base end and the pointed end, and an outlet opening located on the pointed end. At block 2004, the method includes attaching the spike to an inner balloon casing, where the base end of the spike is attached to the inner flexible layer. At block 2006, the method includes locating the spike near an outer balloon casing so that the spike punctures the outer flexible layer in response to the inner flexible layer moving towards the outer flexible layer in response to inflation of a volume of space enclosed by the inner flexible layer. At block 2008, the method includes attaching the outer balloon casing and the inner balloon casing to a catheter tubing connector including a fluid port opening allowing access through the catheter tubing connector to a region between the inner balloon casing and the outer balloon casing, and further including an inflation port allowing access through the catheter tubing connector to the region encased by the inner balloon casing. In an example, the method of manufacturing a balloon catheter system can also include attaching an inner balloon casing to the outer balloon casing in a line parallel to an insertion direction of the balloon catheter.

EXAMPLES

Example 1

This specification generally discloses a fluid delivery device including a spike including a base end and a pointed end, an inlet opening located along the shaft of the spike between the base end and the pointed end, and an outlet opening located on the pointed end; an inner flexible layer, where the base end of the spike is attached to the inner flexible layer; an outer flexible layer, where the spike punctures the outer flexible layer in response to the inner flexible layer moving towards the outer flexible layer in response to inflation of a volume of space enclosed by the inner flexible layer.

The fluid delivery device where the outer flexible layer is blister casing and the inner flexible layer is a balloon casing. The fluid delivery device the blister casing is attached to the balloon casing and encloses a fluid that is ejected through the spike in response to the spike puncturing the blister casing and the volume encased by the blister casing and balloon casing shrinking. The fluid delivery device the volume encased by the blister casing and balloon casing filled with a volume of fluid to prevent the spike to not touch the blister casing until the volume encased by the blister casing and balloon casing deceases. The fluid delivery device where blister casing is an oval shape where the longer side of the oval shape is aligned to be parallel with an insertion direction of the fluid delivery device. The fluid delivery device where the outer flexible layer is an outer balloon casing and the inner flexible layer is an inner balloon casing. The fluid delivery device including a catheter tubing connector to a fluid port opening allowing access through the catheter tubing connector to the region between the inner balloon casing and the outer balloon casing; and an inflation port allowing access through the catheter tubing connector to the region encased by the inner balloon casing. The fluid delivery device including a balloon casing layer attachment joining the inner balloon casing to the outer balloon casing in a line parallel to an insertion direction of the fluid delivery device. The fluid delivery device including a number of balloon casing layer attachments alternatingly located with a row of a number of spikes, where the number of balloon casing layer attachments create a fluid flow channel containing the number of spikes between two balloon casing layer attachments. The fluid delivery device the outer flexible layer is a reverse blister puncture region and the inner flexible layer is a balloon casing attached to a reverse blister casing. The fluid delivery device including an outer balloon casing that encases the reverse blister puncture region, the balloon casing, and the reverse blister casing, where the spike punctures both the reverse blister puncture region and the outer balloon casing in response to inflation of a volume of space enclosed by the inner flexible layer. The fluid delivery device where the spike is aligned with a number of spikes in a row mounted on the inner flexible layer in a direction parallel to an insertion direction of the fluid delivery device. The fluid delivery device including the pointed end of the spike includes a singular point where material forming the spike meets in a single location centrally located from each point along the circumference of the spike shaft, and the outlet opening is located on the pointed end of the spike in a position off-center from the singular point where material forming the spike meets in a single location. The fluid delivery device including the spike in a row of a number of spikes surrounds the circumference of the fluid delivery device. The fluid delivery device including the spike in a row of a number of spikes surrounds a part of the circumference of the fluid delivery device. The fluid delivery device including directional markings on the inner flexible layer indicating an x direction, a y direction, and a z direction of the fluid delivery device. The balloon catheter system including a balloon casing layer attachment joining the inner balloon casing to the outer balloon casing in a line parallel to an insertion direction of the balloon catheter. The system for delivering fluid where the fluid received in the region between the inner balloon casing the outer balloon casing travels through the spike in response to the spike puncturing the outer balloon casing.

Example 2

This specification generally discloses a balloon catheter device, including a spike including a base end and a pointed end, an inlet opening located along the shaft of the spike between the base end and the pointed end, and an outlet opening located on the pointed end; an inner balloon casing, where the base end of the spike is attached to the inner flexible layer; an outer balloon casing, where the spike punctures the outer flexible layer in response to the inner flexible layer moving towards the outer flexible layer in response to inflation of a volume of space enclosed by the inner flexible layer; a catheter tubing connector to a fluid port opening allowing access through the catheter tubing connector to a region between the inner balloon casing and the outer balloon casing, and further including an inflation port allowing access through the catheter tubing connector to the region encased by the inner balloon casing.

The balloon catheter system including a balloon casing layer attachment joining the inner balloon casing to the outer balloon casing in a line parallel to an insertion direction of the balloon catheter. The system for delivering fluid where the fluid received in the region between the inner balloon casing the outer balloon casing travels through the spike in response to the spike puncturing the outer balloon casing.

Example 3

This specification generally discloses a system for delivering fluid to a target area including a catheter tubing with separate channels for a guide wire, inflation, and a fluid; a catheter tubing connector with a separate opening for the guide wire, inflation port, and fluid delivery, where the catheter tubing connector is joined to the catheter tubing with the opening for the guide wire connected to the channel for the guide wire, the opening for the inflation port connected to the inflation channel, and the opening for the fluid delivery connected to the fluid channel; an inner balloon casing with a number of spikes mounted in rows, where the spikes include inlets and outlets on a pointed end of the spike, where the inner balloon casing expands in response to inflation via fluid received through the inflation port opening of the catheter tubing connector; an outer balloon casing that is initially un-punctured and punctured in response to the inflation of a region encased by the inner balloon casing; and where the region between the inner balloon casing the outer balloon casing receives fluid from the opening for fluid delivery of the catheter tubing connector. The system for delivering fluid where the fluid received in the region between the inner balloon casing the outer balloon casing travels through the spike in response to the spike puncturing the outer balloon casing.

Example 4

This specification generally discloses a method of manufacturing a balloon catheter device, including locating an inlet opening and an outlet opening along a spike including a base end and a pointed end, an inlet opening located along the shaft of the spike between the base end and the pointed end, and an outlet opening located on the pointed end. The example method also includes attaching the inner balloon casing, where the base end of the spike is attached to the inner flexible layer. The method also includes locating the spike near an outer balloon casing so that the spike punctures the outer flexible layer in response to the inner flexible layer moving towards the outer flexible layer in response to inflation of a volume of space enclosed by the inner flexible layer. In an example, the method may also include attaching the outer balloon casing and the inner balloon casing to a catheter tubing connector including a fluid port opening allowing access through the catheter tubing connector to a region between the inner balloon casing and the outer balloon casing, and further including an inflation port allowing access through the catheter tubing connector to the region encased by the inner balloon casing. The method can further include a balloon catheter system including attaching an inner balloon casing to the outer balloon casing in a line parallel to an insertion direction of the balloon catheter.

What is claimed is:

1. A fluid delivery device, comprising:
a spike including a base end and a pointed end, an inlet opening located along the shaft of the spike between the base end and the pointed end, and an outlet opening located on the pointed end;
an inner flexible layer, wherein the base end of the spike is attached to the inner flexible layer; and
an outer flexible layer, wherein the spike punctures the outer flexible layer in response to the inner flexible layer moving towards the outer flexible layer in response to inflation of a volume of space enclosed by the inner flexible layer, wherein the outer flexible layer is blister casing and the inner flexible layer is a balloon casing.

2. The fluid delivery device of claim 1, wherein the blister casing is attached to the balloon casing and encloses a fluid that is ejected through the spike in response to the spike puncturing the blister casing and the volume encased by the blister casing and balloon casing shrinking.

3. The fluid delivery device of claim 2, wherein the volume encased by the blister casing and balloon casing filled with a volume of fluid to prevent the spike to not touch the blister casing until the volume encased by the blister casing and balloon casing deceases.

4. The fluid delivery device of claim 1, wherein blister casing is an oval shape where the longer side of the oval shape is aligned to be parallel with an insertion direction of the fluid delivery device.

5. The fluid delivery device of claim 1, wherein the spike is aligned with a plurality of spikes in a row mounted on the inner flexible layer in a direction parallel to an insertion direction of the fluid delivery device.

6. The fluid delivery device of claim 1, comprising:
the pointed end of the spike includes a singular point where material forming the spike meets in a single location centrally located from each point along the circumference of the spike shaft, and
the outlet opening is located on the pointed end of the spike in a position off-center from the singular point where material forming the spike meets in a single location.

7. The fluid delivery device of claim 1, comprising the spike in a row of a plurality of spikes surrounds the circumference of the fluid delivery device.

8. The fluid delivery device of claim 1, comprising the spike in a row of a plurality of spikes surrounds a part of the circumference of the fluid delivery device.

9. The fluid delivery device of claim 1, comprising directional markings on the inner flexible layer indicating an X direction, a Y direction, and a Z direction of the fluid delivery device.

10. A method of manufacturing a balloon catheter device, comprising:
locating an inlet opening and an outlet opening along a spike including a base end and a pointed end, an inlet opening located along the shaft of the spike between the base end and the pointed end, and an outlet opening located on the pointed end;
attaching the spike to an inner balloon casing, where the base end of the spike is attached to the inner flexible layer;
locating the spike near an outer balloon casing so that the spike punctures the outer flexible layer in response to the inner flexible layer moving towards the outer flexible layer in response to inflation of a volume of space enclosed by the inner flexible layer;
attaching the outer balloon casing and the inner balloon casing to a catheter tubing connector including a fluid port opening allowing access through the catheter tubing connector to a region between the inner balloon casing and the outer balloon casing, and further including an inflation port allowing access through the catheter tubing connector to the region encased by the inner balloon casing.

11. The method of manufacturing a balloon catheter system of claim 10, comprising attaching an inner balloon casing to the outer balloon casing in a line parallel to an insertion direction of the balloon catheter.

12. A system for delivering fluid to a target area comprising:
a catheter tubing with separate channels for a guide wire, inflation, and a fluid;
a catheter tubing connector with a separate opening for the guide wire, inflation port, and fluid delivery, wherein the catheter tubing connector is joined to the catheter tubing with the opening for the guide wire connected to the channel for the guide wire, the opening for the inflation port connected to the inflation channel, and the opening for the fluid delivery connected to the fluid channel;
an inner balloon casing with a plurality of spikes mounted in rows, wherein the spikes include inlets and outlets on a pointed end of the spike, wherein the inner balloon casing expands in response to inflation via fluid received through the inflation port opening of the catheter tubing connector;
an outer balloon casing that is initially un-punctured and punctured in response to the inflation of a region encased by the inner balloon casing; and
wherein the region between the inner balloon casing the outer balloon casing receives fluid from the opening for fluid delivery of the catheter tubing connector.

13. The system for delivering fluid of claim 12, wherein the fluid received in the region between the inner balloon casing and the outer balloon casing travels through the spike in response to the spike puncturing the outer balloon casing.

14. A fluid delivery device, comprising:
- a spike including a base end and a pointed end, an inlet opening located along the shaft of the spike between the base end and the pointed end, and an outlet opening located on the pointed end;
- an inner flexible layer, wherein the base end of the spike is attached to the inner flexible layer; and
- an outer flexible layer, wherein the spike punctures the outer flexible layer in response to the inner flexible layer moving towards the outer flexible layer in response to inflation of a volume of space enclosed by the inner flexible layer, wherein the outer flexible layer is an outer balloon casing and the inner flexible layer is an inner balloon casing.

15. The fluid delivery device of claim 14, comprising a catheter tubing connector with a fluid port opening allowing access through the catheter tubing connector to the region between the inner balloon casing and the outer balloon casing, the catheter tubing connector also with an inflation port allowing access through the catheter tubing connector to the region encased by the inner balloon casing.

16. The fluid delivery device of claim 14, comprising a balloon casing layer attachment joining the inner balloon casing to the outer balloon casing in a line parallel to an insertion direction of the fluid delivery device.

17. The fluid delivery device of claim 16, comprising a plurality of balloon casing layer attachments alternatingly located with a row of a plurality of spikes, wherein the plurality of balloon casing layer attachments create a fluid flow channel containing the plurality of spikes between two balloon casing layer attachments.

18. A fluid delivery device, comprising:
- a spike including a base end and a pointed end, an inlet opening located along the shaft of the spike between the base end and the pointed end, and an outlet opening located on the pointed end;
- an inner flexible layer, wherein the base end of the spike is attached to the inner flexible layer; and
- an outer flexible layer, wherein the spike punctures the outer flexible layer in response to the inner flexible layer moving towards the outer flexible layer in response to inflation of a volume of space enclosed by the inner flexible layer, wherein the outer flexible layer is a reverse blister puncture region and the inner flexible layer is a balloon casing attached to a reverse blister casing.

19. The fluid delivery device of claim 18, comprising an outer balloon casing that encases the reverse blister puncture region, the balloon casing, and the reverse blister casing, wherein the spike punctures both the reverse blister puncture region and the outer balloon casing in response to inflation of a volume of space enclosed by the inner flexible layer.

* * * * *